US012637416B1

(12) United States Patent
Nag et al.

(10) Patent No.: US 12,637,416 B1
(45) Date of Patent: May 26, 2026

(54) HALOGENATED BENZYLIDINE DERIVATIVES

(71) Applicant: Renovel Innovations, Inc., Fremont, CA (US)

(72) Inventors: Bishwajit Nag, Union City, CA (US); Ananda Sen, Castro Valley, CA (US); Nitish Nag, Union City, CA (US); Arjun Sanyal, Castro Valley, CA (US); Srinivasan Narasimhan, Chennai (IN)

(73) Assignee: Renovel Innovations, Inc., Fremont, CA (US)

( * ) Notice: Subject to any disclaimer, the term of this patent is extended or adjusted under 35 U.S.C. 154(b) by 0 days.

(21) Appl. No.: 19/275,436

(22) Filed: Jul. 21, 2025

Related U.S. Application Data

(63) Continuation-in-part of application No. 18/942,833, filed on Nov. 11, 2024, which is a continuation of application No. 17/584,189, filed on Jan. 25, 2022, now Pat. No. 12,195,418.

(60) Provisional application No. 63/141,880, filed on Jan. 26, 2021.

(51) Int. Cl.

| | |
|---|---|
| ***C07D 213/74*** | (2006.01) |
| ***C07C 229/36*** | (2006.01) |
| ***C07C 251/24*** | (2006.01) |
| ***C07D 213/80*** | (2006.01) |

(52) U.S. Cl.
CPC .......... *C07C 251/24* (2013.01); *C07C 229/36* (2013.01); *C07D 213/74* (2013.01); *C07D 213/80* (2013.01)

(58) Field of Classification Search
CPC .. C07D 213/74; C07D 213/80; C07C 251/24; C07C 229/36
See application file for complete search history.

(56) References Cited

U.S. PATENT DOCUMENTS

| | | | | |
|---|---|---|---|---|
| 10,577,313 | B2 * | 3/2020 | Yasumura | B01J 31/04 |
| 12,195,418 | B2 * | 1/2025 | Nag | C07C 229/36 |

OTHER PUBLICATIONS

Tian, Appl Organometal Chem, 2005, vol. 19, 980-987. (Year: 2005).*

* cited by examiner

*Primary Examiner* — D Margaret M Seaman
(74) *Attorney, Agent, or Firm* — Adam Warnick Bell; Gregory Scott Smith; Matthew Kaser

(57) ABSTRACT

Halogenated Benzylidine derivatives which exhibit activity useful for the treatment of immunological diseases and inflammation.

11 Claims, 29 Drawing Sheets

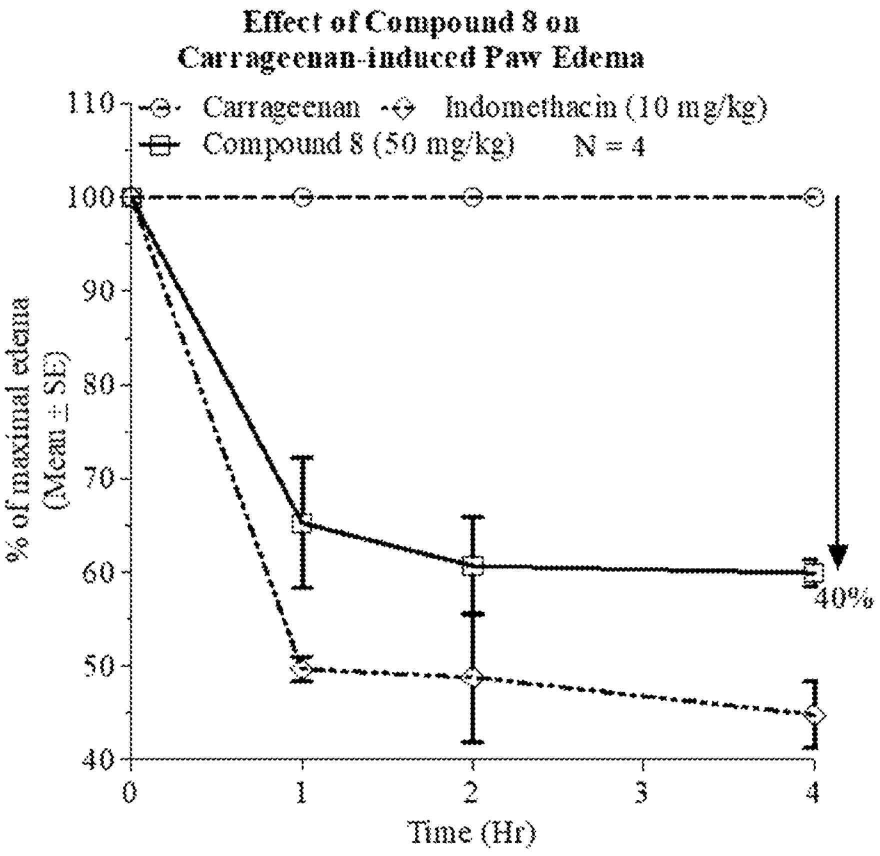
FIG.1 (e2924)

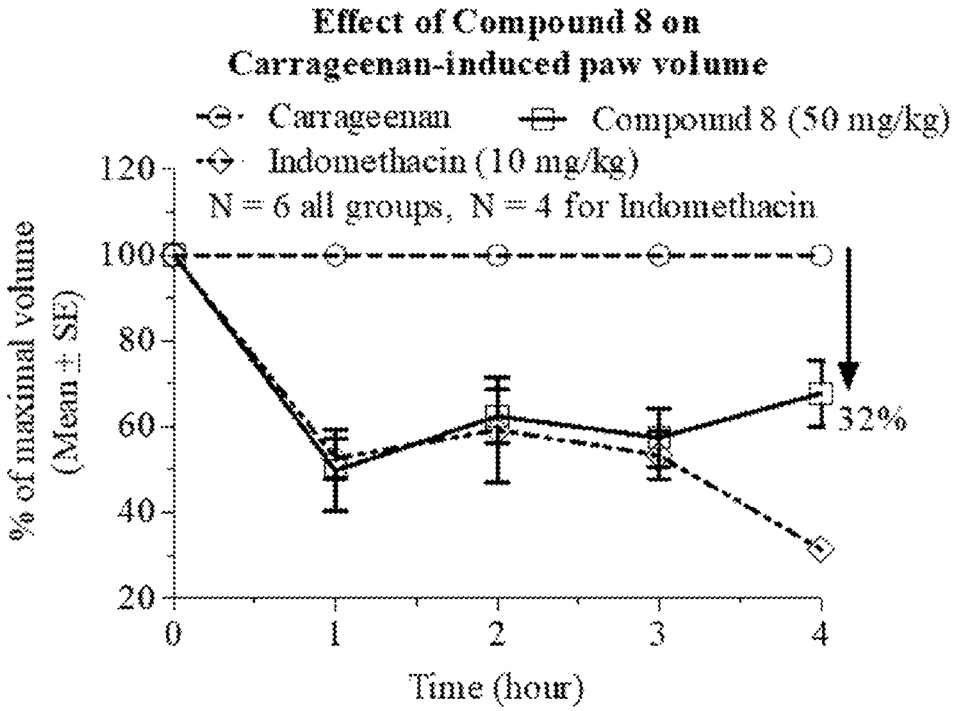
FIG.2 (e29 26A)
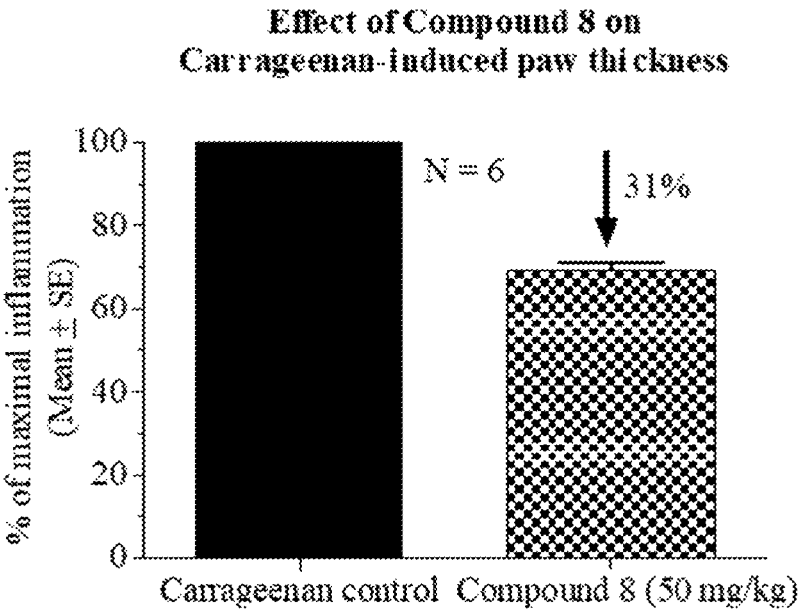
FIG.3 (e29 26B)

FIG.3 (e29 26B)
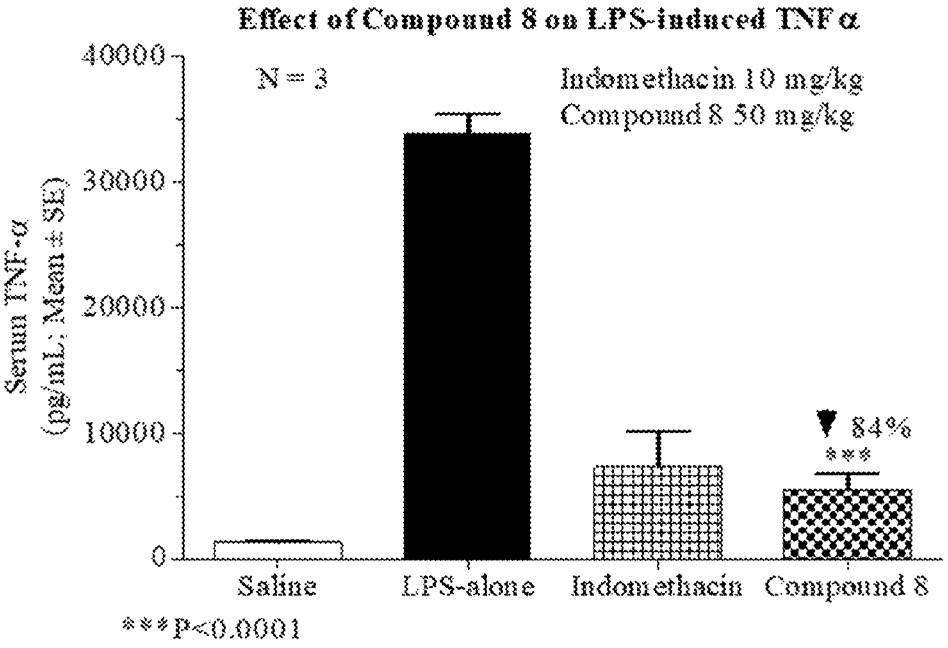
FIG.4 (e2929A)
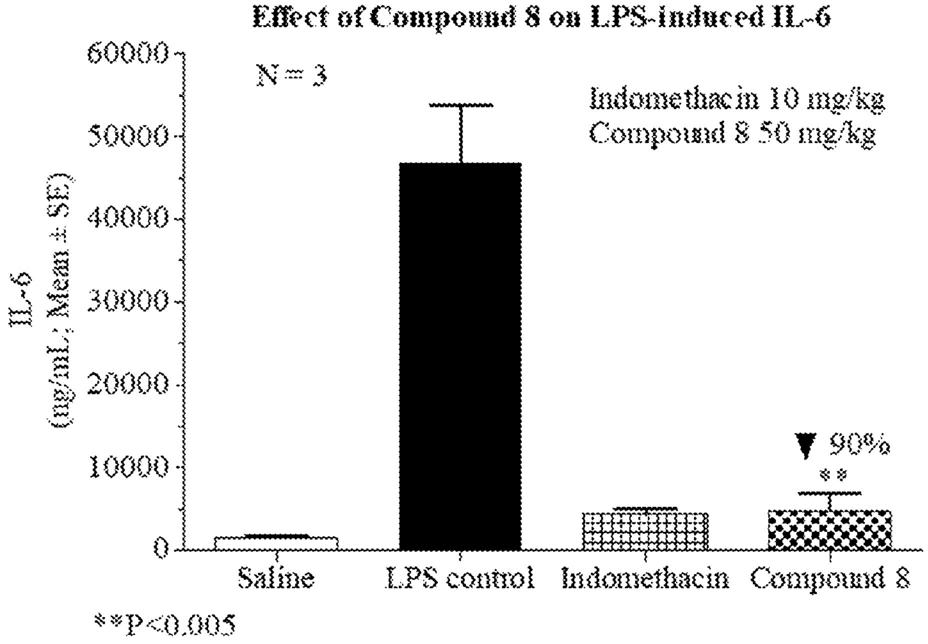
FIG.5 (e2929B)

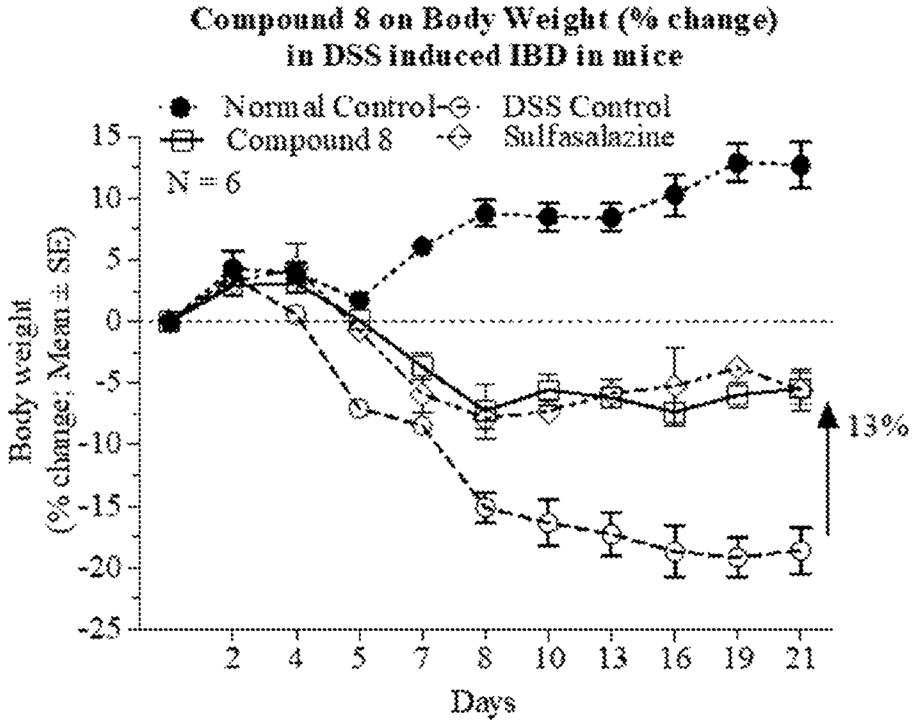
FIG. 6 (e2930)

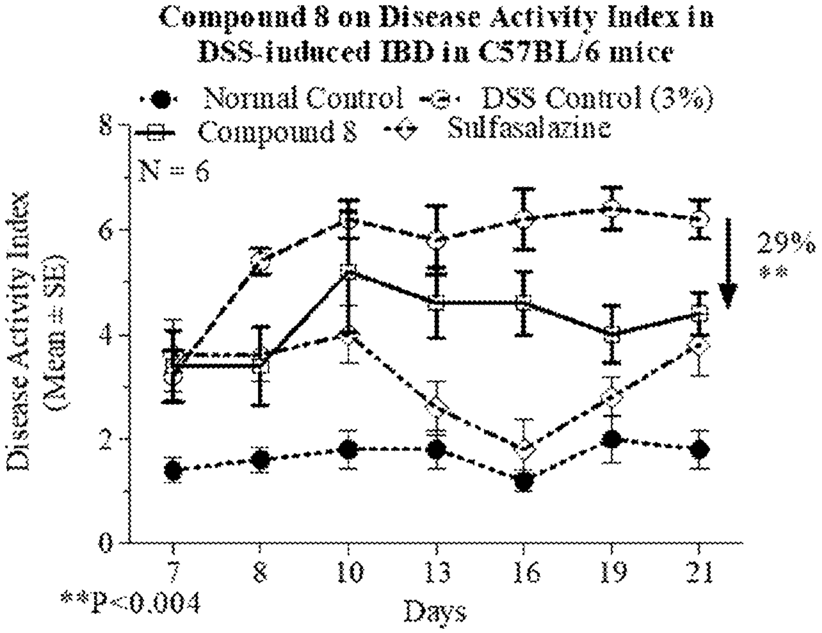
FIG.7 (e2931)
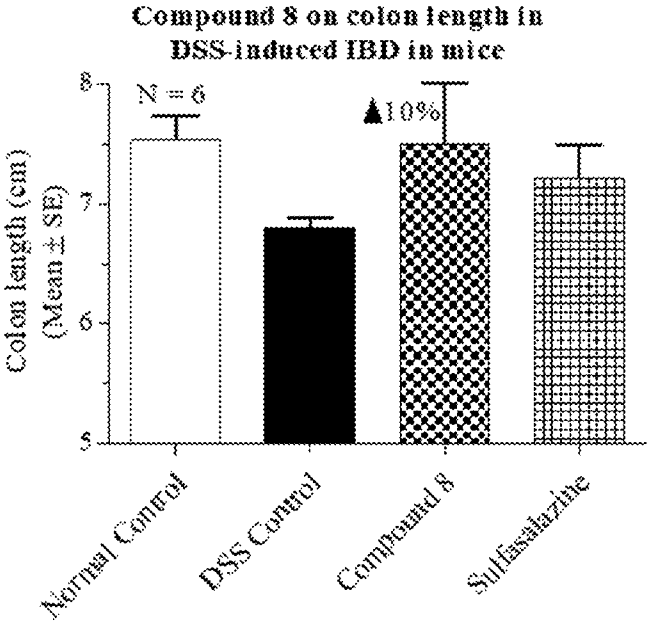
FIG.8 (e2932)

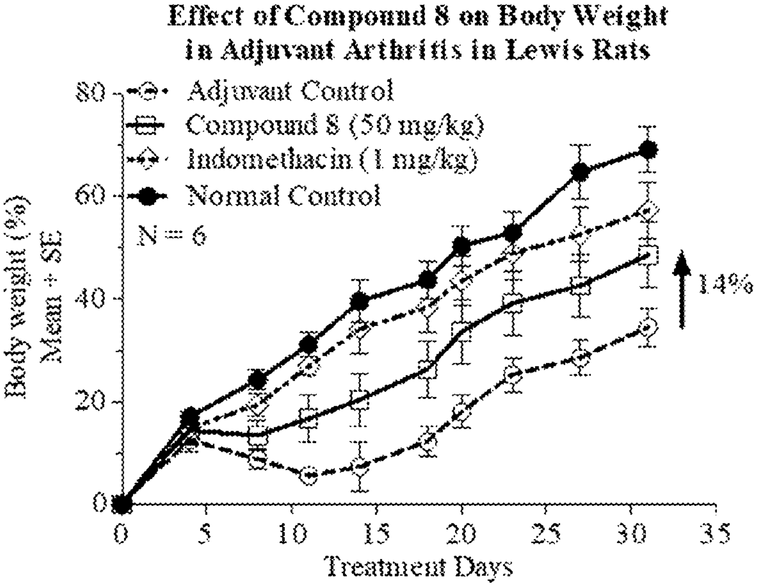
FIG.9
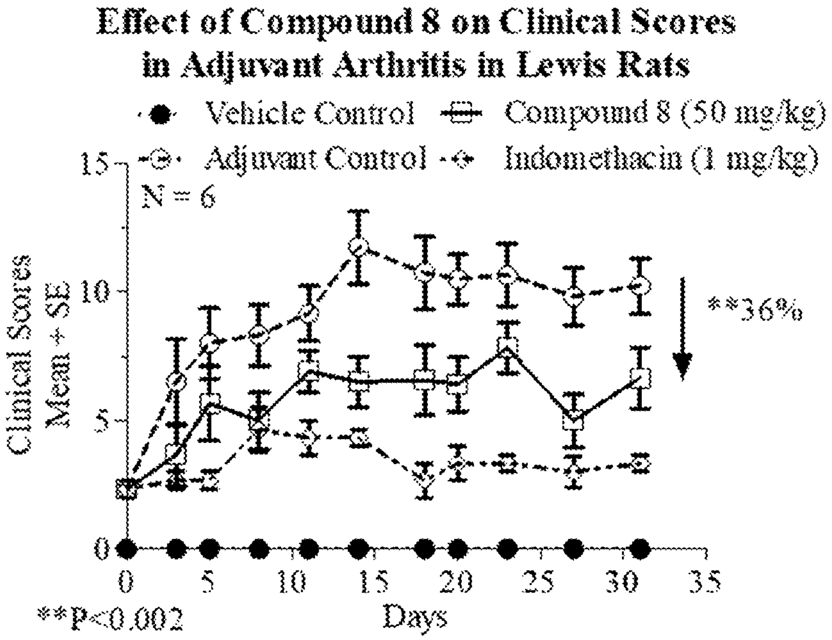
FIG.10 (e2933)

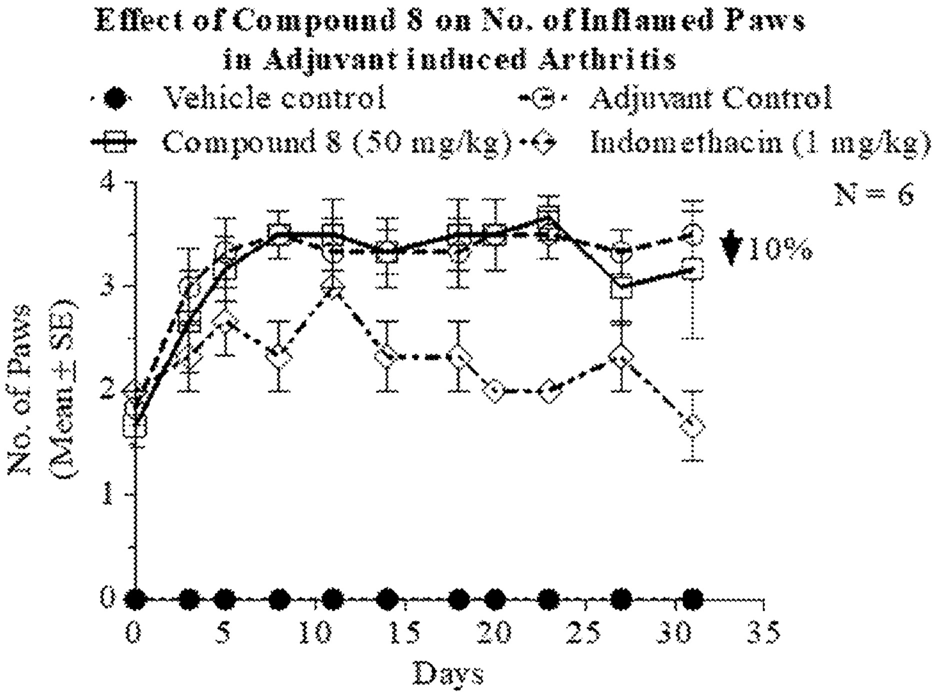
FIG.11 (e2934)

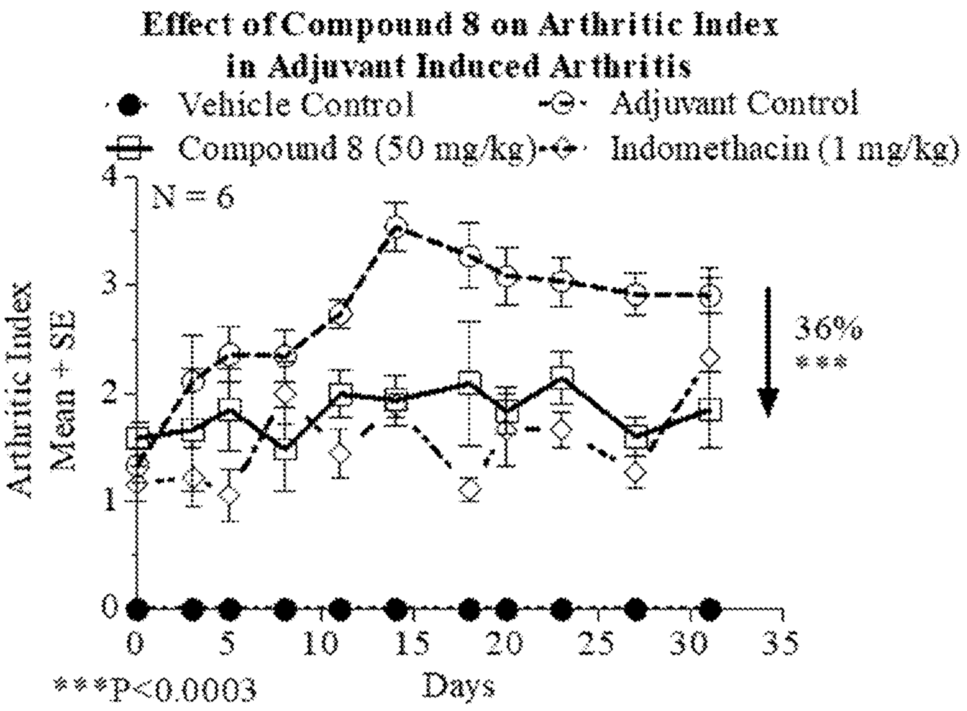
FIG.12 (e2935)
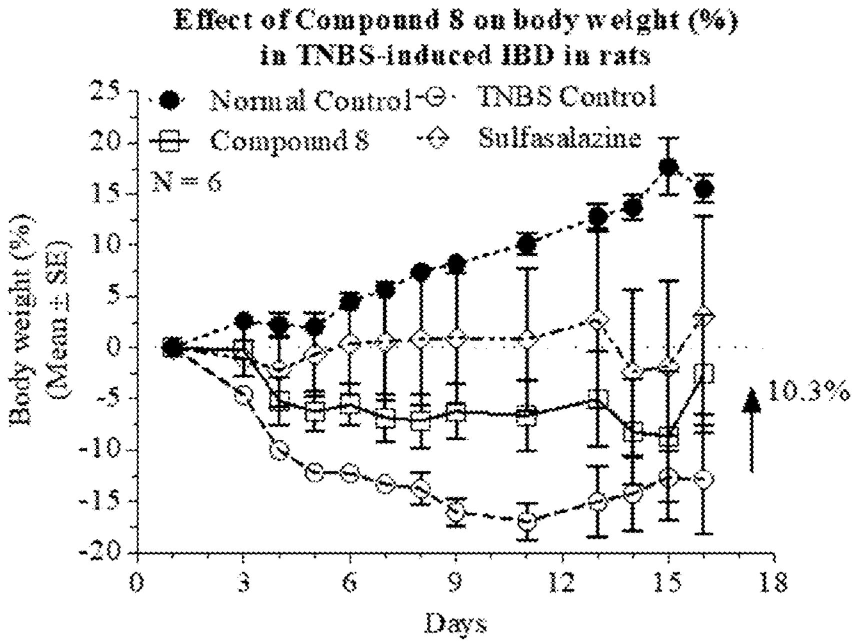
FIG.13

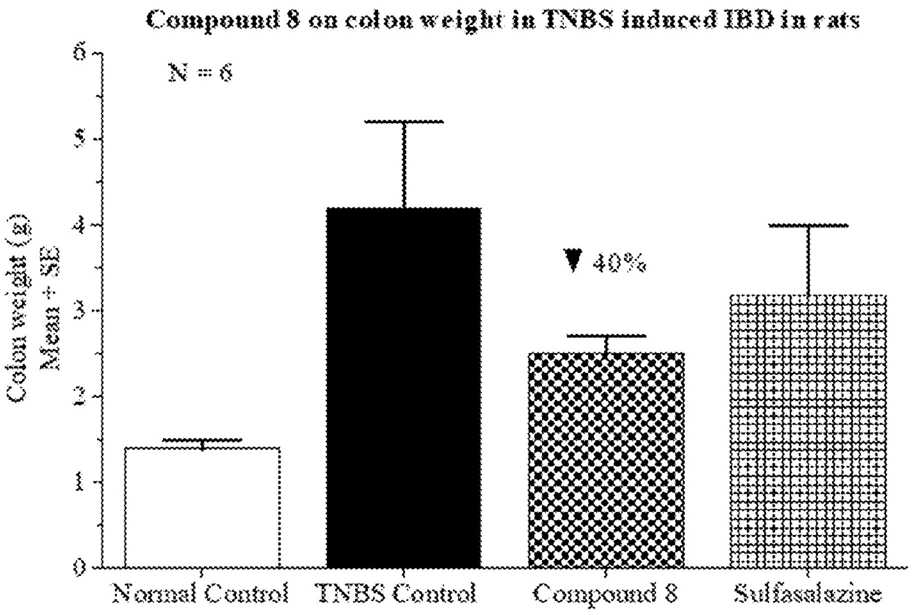
FIG.14 (from "Figs of compound 8…)
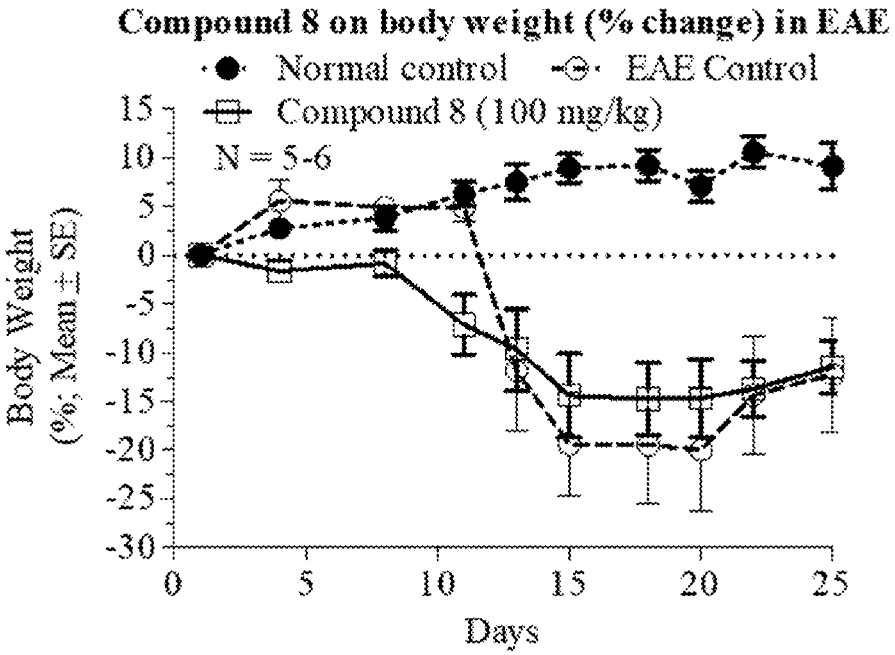
FIG.15 (e299A "Figs of compound 8…)

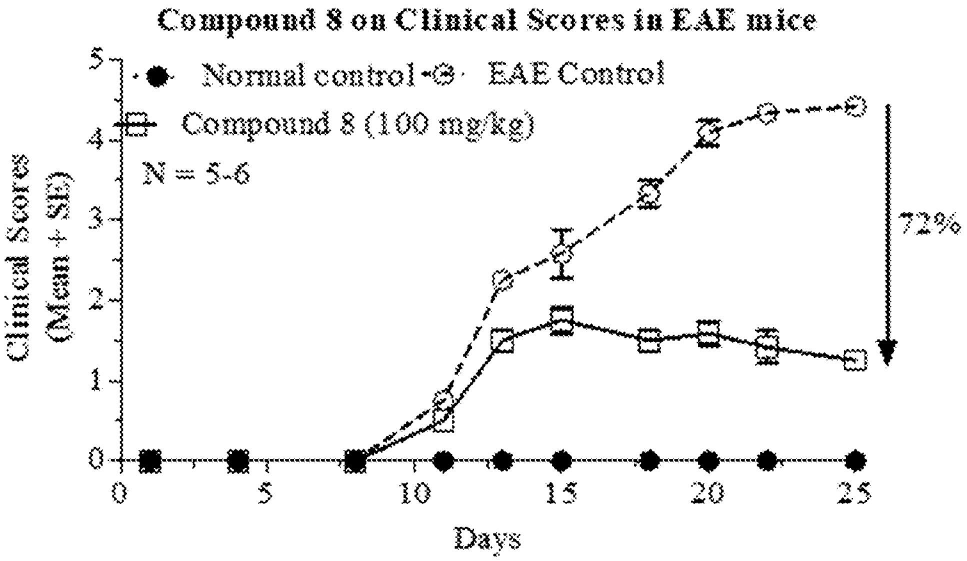
| Score | Clinical Findings |
|---|---|
| 1 | Loss of tail tonicity |
| 1.5 | Hind limb inhibition |
| 2 | Hind limb dragging + limp tail |
| 2.5 | Hind limb inhibition + limp tail |
| 3 | Partial hind limb paralysis |
| 3.5 | Complete hind limb paralysis |
| 4 | Hind and front limb paralysis |
| 4.5 | Complete paralysis + no movement |
| 5 | Moribund |
FIG.16 (e2910 “Figs of compound 8…)

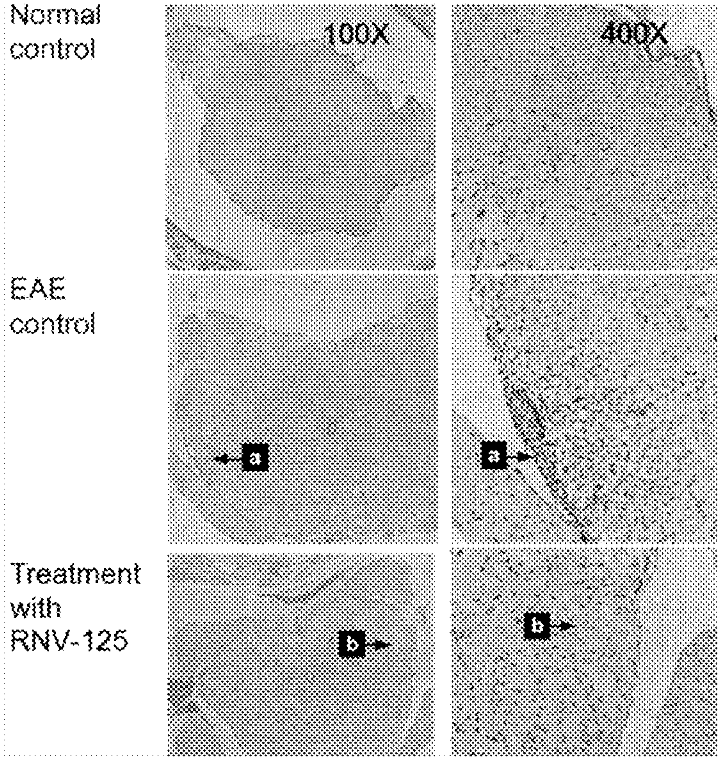
FIG. 17 (e2911)

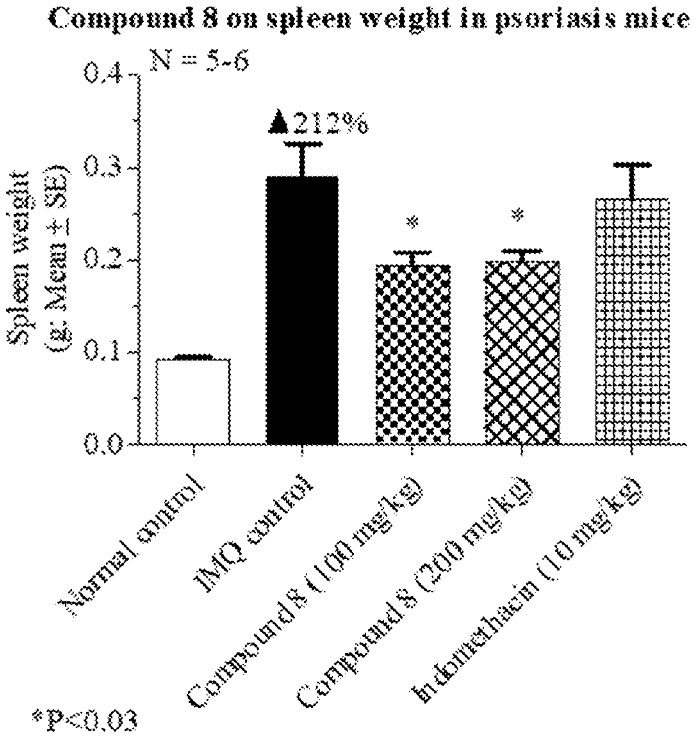
FIG.22 (e2914B)

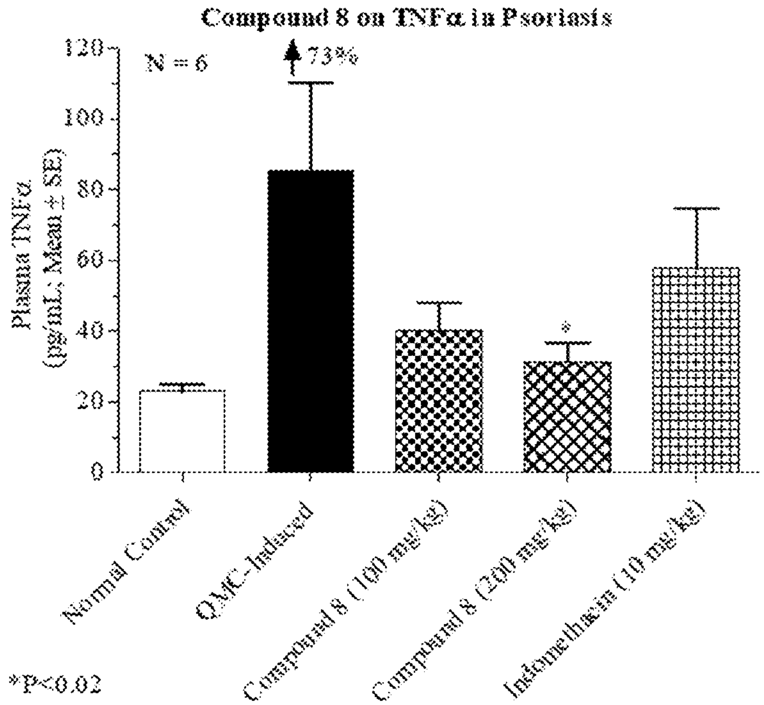
FIG.23 (e2915)
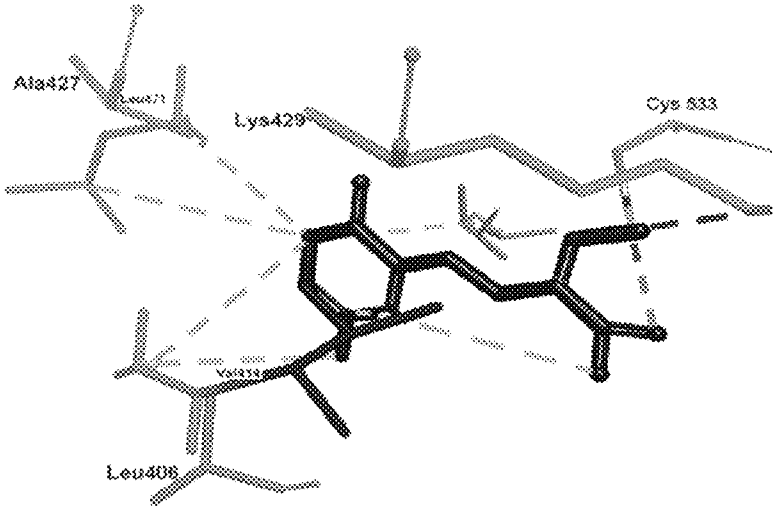
FIG.24 (e2920)

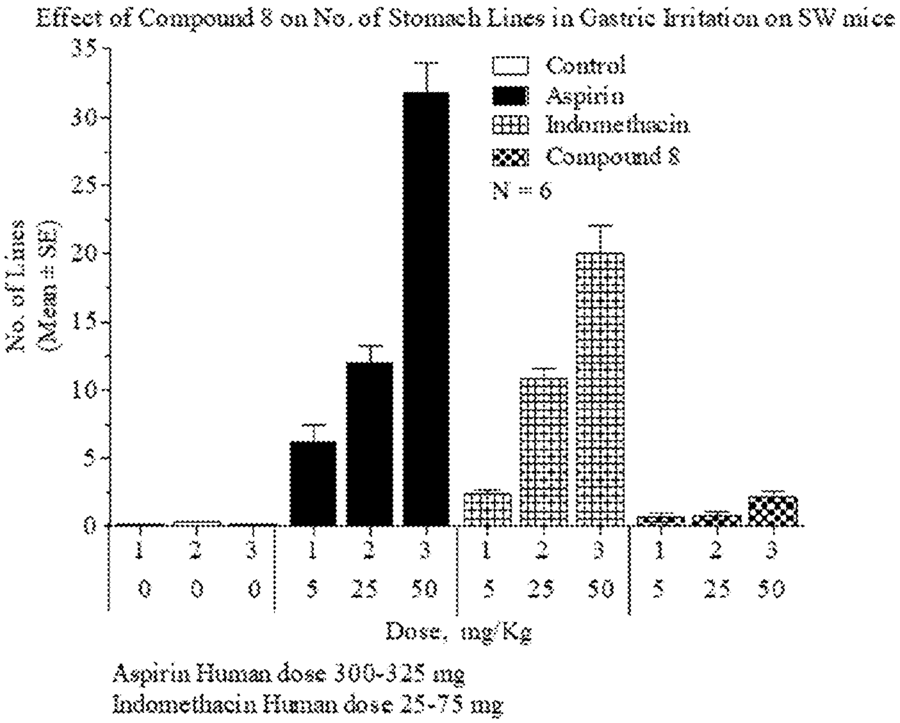
FIG.25 (e2921A)
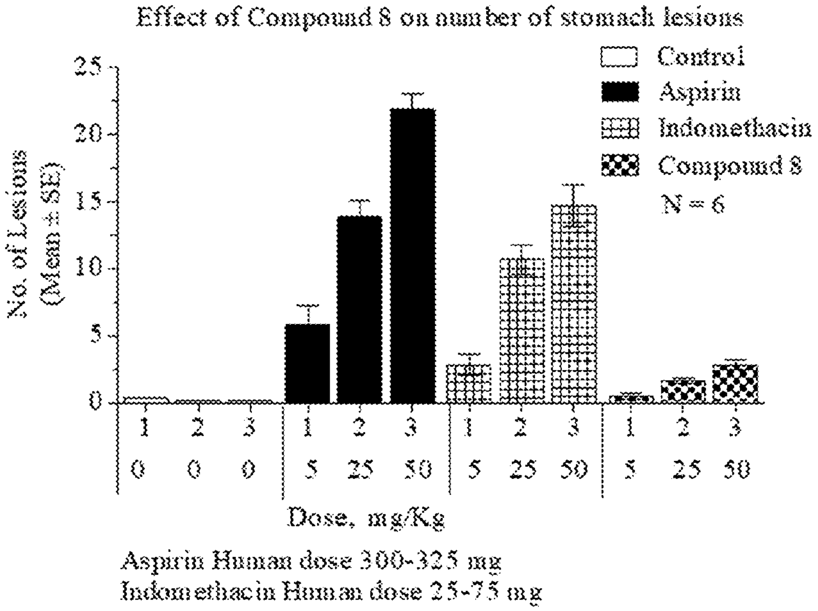
FIG.26 (e2921B)

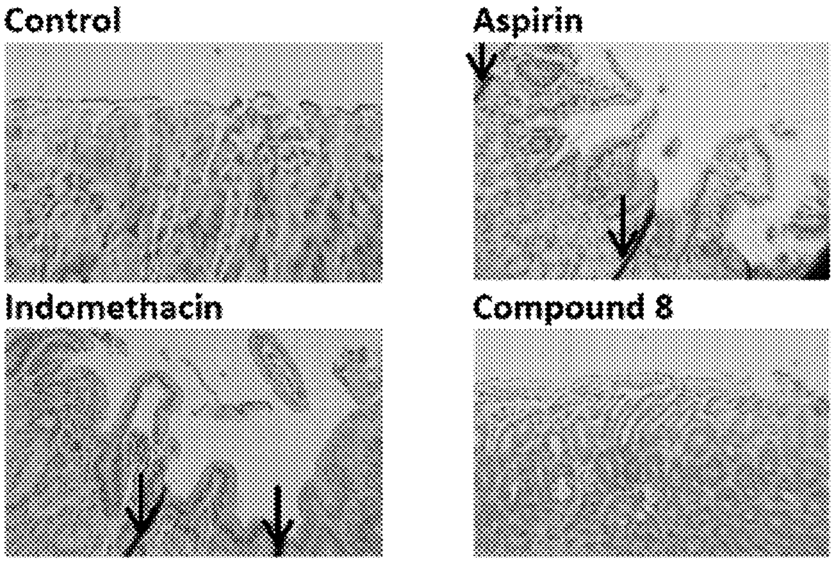
FIG.27 (e2922)
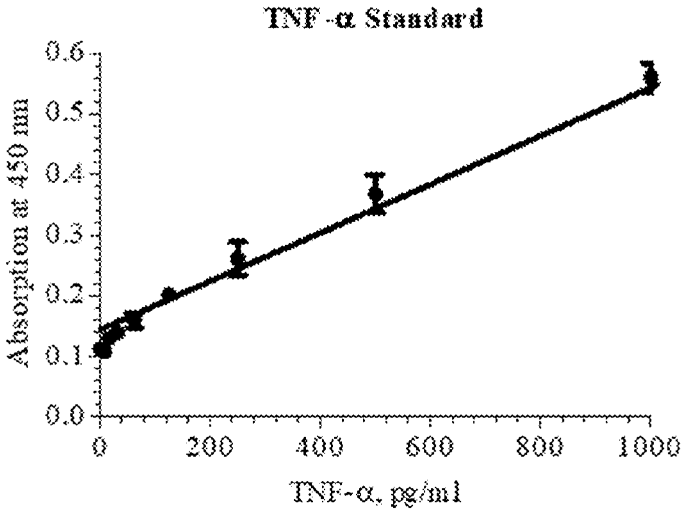
Fig. 28A

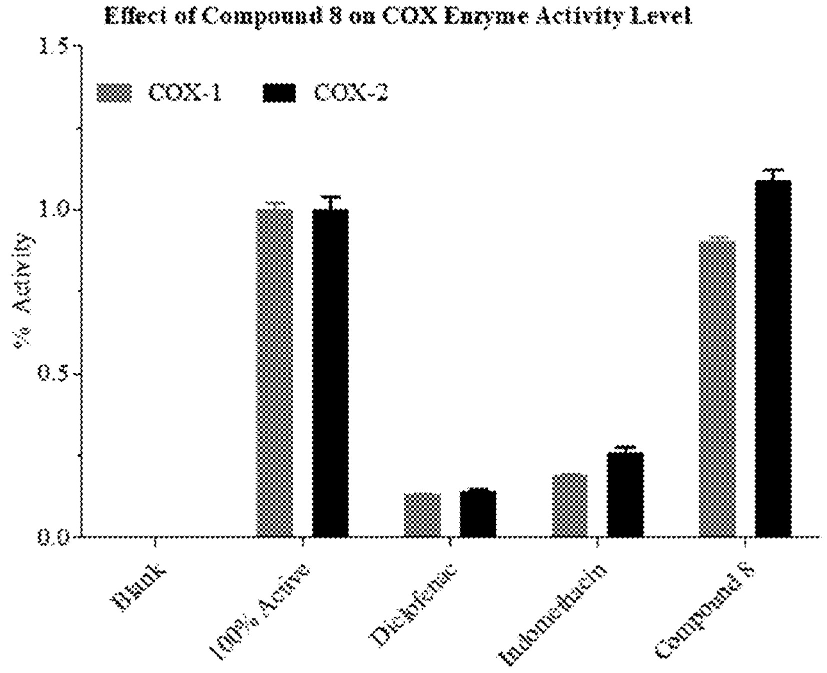
FIG.31A
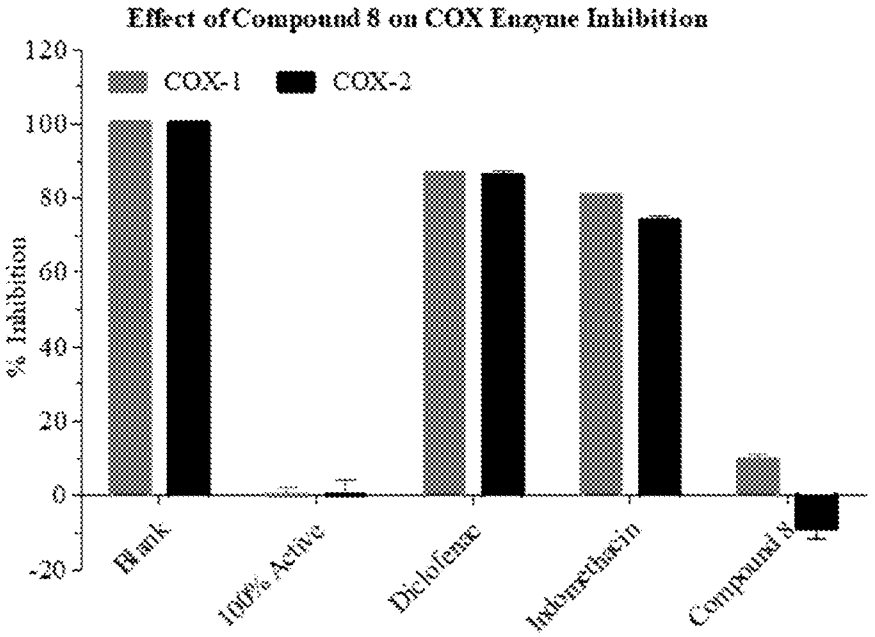
FIG. 31B (from study report 157)

| Table: Values for the strongest binding confirmations between RNV-125 and eight macromolecules involved in the regulation of IL-6 production | | |
|---|---|---|
| Macromolecule Receptor | RCSB ID | Highest Binding Affinity |
| ERK-1 | 4QTB | -7.6 kcal/mol |
| NIK | 4DN5 | -7.5 kcal/mol |
| ERK-2 | 5NHJ | -7.1 kcal/mol |
| MEK ½ | 4U7Z | -6.8 kcal/mol |
| IKKβ | 4KIK | -6.5 kcal/mol |
| SHP-1 | 2B3O | -6.4 kcal/mol |
| Raf-1 | 3OMV | -6.2 kcal/mol |
| TLR-4 | 3FXI | -5.9 kcal/mol |

| Table: Binding affinities of RNV-125 and existing NIK Inhibitor SMI1 at two binding regions | | |
|---|---|---|
| Molecule | Binding Affinity (BA) at Site 1 | Binding Affinity (BA) at Site 2 |
| RNV-125 | -7.5 kcal/mol | -7.0 kcal/mol |
| NIK Inhibitor SMI1 | -8.0 kcal/mol | -7.3 kcal/mol |

FIG. 32

| | |
|---|---|
| 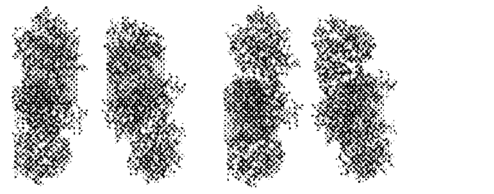 | 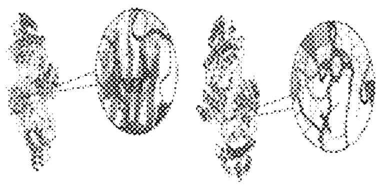 |
| Stick Structure of Human NF-kappaB inducing kinase (NIK), PDB entry 4G3D | Modeled structure of NIK interacting with RNV-125 molecules |
| 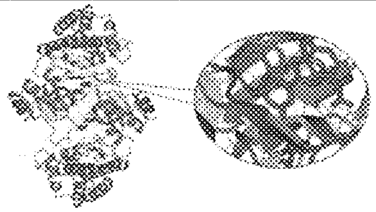 | 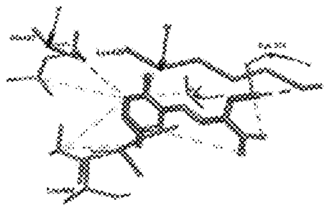 |
| Crystal structure of NIK interacting with RNV-125 molecule and two NIK inhibitors | Virtual docking poses of identified compounds and RNV- 125 |
FIG. 33
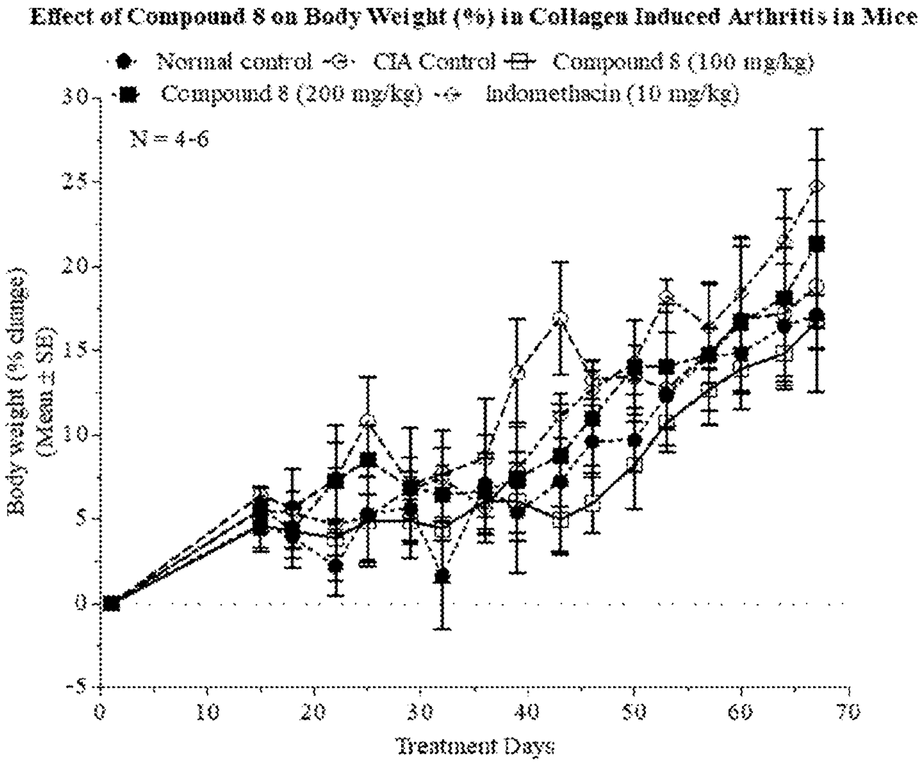
FIG. 34

HALOGENATED BENZYLIDINE DERIVATIVES

RELATIONSHIP TO OTHER APPLICATIONS

This application is a continuation-in part of Ser. No. 18/942,833 that was filed Nov. 11, 2024, and Ser. No. 18/942,833 is a continuation of Ser. No. 17/584,189, filed on 25 Jan. 2022, which was patented as U.S. Pat. No. 12,195,418 on 14 Jan. 2025. Ser. No. 17/584,189 claims the benefit of and priority to U.S. Provisional Application No. 63/141,880 filed 26 Jan. 2021, which are all incorporated herein by reference.

GOVERNMENT SUPPORT

None

FIELD OF THE INVENTION

The present invention relates to novel halogenated benzylidene derivatives for the treatment of immunological diseases, autoimmune disorders, and inflammation.

BACKGROUND OF INVENTION

Inflammation is part of the complex biological response of vascular tissues to harmful stimuli, such as pathogens, damaged cells, or irritants. The classical signs of acute inflammation are pain, heat, redness, swelling, and loss of function. Inflammation is a protective attempt by the organism to remove the injurious stimuli and to initiate the healing process. Inflammation is not a synonym for infection, even in cases where inflammation is caused by infection. Progressive destruction of the tissue would compromise the survival of the organism.

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process. Chronic inflammation can also lead to a host of diseases, such as hayfever, periodontitis, atherosclerosis, rheumatoid arthritis, and even cancer (e.g., gallbladder carcinoma).

The compounds and compositions of the present invention are used to treat diseases associated with Inflammation, which include (but are not limited to) the following: Chron's Disease, Appendicitis, Bursitis, Colitis, Cystitis, Dermatitis, Epididymitis, Gingivitis, Meningitis, Myelitis, Nephritis, Neuritis, Pancreatitis, Periodontitis, Pharyngitis, Phlebitis, Prostatitis, Sinusitis, Tendonitis, Tonsillitis, Urethritis, Vasculitis, Vaginitis, Rheumatoid Arthritis, Osteoarthritis, Psoriatic Arthritis, Septic Arthritis, Chronic Inflammation, Asthma, Hepatitis, Laryngitis, Thyroiditis, Lymphangitis, Gout, Arteritis, Bronchitis, Acne Vulgaris, Pneumonia, Sarcoidosis, Endocarditis, Myocarditis, Pericarditis, Duodenitis, Esophagitis, Folliculitis, Anaemia, Hypersensitivity, Chronic Obstructive Pulmonary Disease, Complex Regional Pain Syndrome, Rhinitis and Celiac Disease.

SUMMARY OF INVENTION

The present invention relates to novel Halogenated Benzylidene derivatives of the formula (I)

Formula I

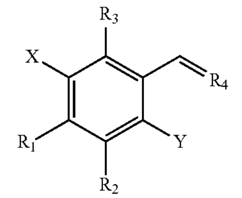

their derivatives, analogues, tautomeric forms, stereoisomers, their polymorphs, pharmaceutically acceptable salts, and pharmaceutically acceptable solvates, wherein X corresponds to any halogen; Y corresponds to hydrogen, any halogen, hydroxyl, alkoxy, nitro, amino or sulphonyl groups; $R_1$ and $R_3$ corresponds to any of H, OH or alkyl chain with any number of carbon atoms or modifications therein; $R_2$ corresponds to a Hydrogen or hydroxyl, a free hydroxyl group or extended chain through an alkyloxy ester or un-substituted or substituted aryloxy ester groups; $R_4$ corresponds to any naturally occurring or synthesized amino acid, their derivatives like amino acid alcohol and amino acid ester, condensed through their free amino group. Also, $R_4$ may correspond to an un-substituted or substituted aryl amine, pyridyl amine or amino benzoic acid wherein the free amine group condenses to form a halogenated benzylidene compound. Compounds derived from the saturation of the double bond to $R_4$ are also included.

More specifically, the present invention relates to a molecule designated by the applicants as "RNV-125", also referred to as "COMPOUND 8", having the IUPAC name:

4-Bromo-2-[(1-hydroxymethyl-2-methyl-propylimino)-methyl]-phenol and having the structural formula:

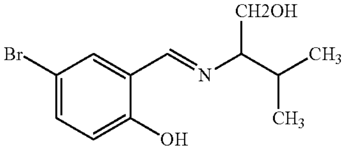 [SMILES: CC(C)C(CO)/N=C/c1cc(Br)ccc1O]

Note the —$CH_2OH$ hydroxymethyl group attached to N.

The present invention also relates to a process for the preparation and the therapeutic use of any of said novel compounds or their analogues, their tautomeric forms etc.

Additionally, the present invention relates to a molecule structurally similar to RVN-125, which has been designated by the applicants as RNV-124 also referred to as "COMPOUND 7", having the IUPAC name:

2-[(5-Bromo-2-hydroxy-benzylidene)-amino]-3-methyl-butyric acid and having the structural formula:

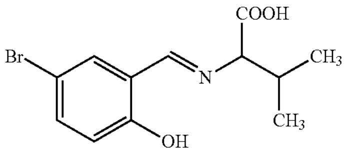

Note the —COOH carboxyl group attached to N.

BRIEF DESCRIPTION OF FIGURES

The original graphs and figures may include colour, which is not shown in this disclosure, but will be made available to the office if requested. The colours are generally represented in the greyscale images by different shades of grey and the meaning of the shading can generally be extrapolated and understood in context.

FIG. 1 shows that the group of rats administered with Compound 8 (RNV-125) exhibited a 40% decrease in carrageenan-induced inflammation.

FIG. 2 shows that the group of rats administered with Compound 8 (RNV-125) showed a 32% decrease in carrageenan-induced inflammation.

FIG. 3 The group of rats administered with Compound 8 (RNV-125) showed a 31% decrease in carrageenan-induced paw thickness.

FIG. 4 shows that the group of mice administered with Compound 8 (RNV-125) showed an 84% decrease in LPS-induced TNF-α (P<0.0001).

FIG. 5 shows that the group of mice administered with Compound 8 (RNV-125) showed a 90% decrease in IL-6 from the LPS group (P<0.005).

FIG. 6 shows that at the end of the study period of 21 days, the group of mice administered with Compound 8 (RNV-125) showed an increase by 13% in body weight, compared with the vehicle in DSS-induced IBD group.

FIG. 7 shows that at the end of the study period of 21 days, the group of mice administered with Compound 8 (RNV-125) showed a significant (P<0.004) decrease by 29% in Disease Activity Index, compared with the vehicle DSS-induced IBD group.

FIG. 8 shows that at the end of the study period of 21 days, the group of mice administered with Compound 8 (RNV-125) showed a 10% increase in colon length, compared with the vehicle DSS-induced IBD group.

FIG. 9 shows that at the end of the study period of 30 days, the group of rats administered with Compound 8 (RNV-125) showed a significant (P<0.02) decrease by 41%, from the vehicle control group in clinical scores FIG. 10 shows that at the end of the study period of 30 days, the group of rats administered with Compound 8 (RNV-125) showed a significant (P<0.002) decrease by 36%, from the vehicle control group in clinical scores in AIA-induced arthritis FIG. 11 shows that at the end of the study period of 30 days, the group of rats administered with Compound 8 (RNV-125) showed a decrease by 10% in their number of limbs showing arthritic symptoms, from the vehicle control group in AIA-induced arthritis FIG. 12 shows that at the end of the study period of 30 days, the group of rats administered with Compound 8 (RNV-125) showed a significant (P<0.0003) decrease by 36% in their Arthritic Index, from the vehicle control group in AIA-induced arthritis.

FIG. 13 shows the that Compound 8 (TNV-125) decreases body weight by 10.3% in the TNBS-induced mice.

FIG. 14 shows that treatment with Compound 8 (RNV-125) at 50 mg/kg reversed the TNBS-induced increase in colon weight by 40%.

FIG. 15 shows the effect of Compound 8 (TNV-125) on body weight in EAE mice.

FIG. 16 shows an increase of clinical scores in the EAE control group of mice. Compound 8 (RNV-125) at 100 mg/kg produced a 72% decrease of clinical scores when compared with the EAE control group of mice.

FIG. 17 shows the histological evaluation of the spinal cords having a presence of inflammatory infiltrate in the periphery in the EAE control group mice. Treatment with Compound 8 (RNV-125) showed a decrease in the infiltrate.

FIG. 22 shows a 212% increase in spleen weight in the IMQ control group of psoriatic mice compared with the normal control group of mice. Treatment with Compound 8 (RNV-125) at 100 and 200 mg/kg significantly (P<0.03) reversed the increase in spleen weights in the IMQ control group of mice.

FIG. 23 shows that Compound 8 (RNV-125) at 200 mg/kg shows a significant decrease (P<0.02) in plasma TNF-α in psoriatic mice.

FIG. 24 shows the virtual docking poses of identified compounds and RNV-125

FIG. 25 shows the lines in the gastric mucosa of male Swiss Webster mice treated with Compound 8 (RNV-125) at 5 mg/kg, 25 mg/kg, and 50 mg/kg po.

FIG. 26 shows the lesions in the gastric mucosa of male Swiss Webster mice treated with Compound 8 (RNV-125) at 5 mg/kg, 25 mg/kg, and 50 mg/kg showing lesions were comparable to the untreated mice.

FIG. 27 shows the histopathology of male Swiss Webster mice treated with Aspirin, Indomethacin, and Compound 8 (RNV-125). The gastric mucosa of the mice treated with aspirin and indomethacin show the lines whereas the gastric mucosa of mice treated with Compound 8 at 50 mg/kg is comparable to the control.

FIG. 28A shows the effect of RNV-125 on TNF-α with its corresponding standard curve.

FIG. 31 shows effect of Compound 8 (RNV-125) on COX-1 and COX-2 enzyme activity (31A) and inhibition (31B). RNV-125 reduced the activity of COX-1 by about 10%. No reduction of COX-2 was observed with RNV-125.

FIG. 32 shows the binding confirmations between Compound 8 (RNV-125) and 8 macromolecules involved in the regulation of IL-6 production. Also the binding affinities of Compound 8 (RNV-125) and existing NIK inhibitor SMI1 at 2 binding regions FIG. 33 shows Compound 8 (RNV-125) interacting with the model and crystal structures of NIK FIG. 34 shows the effect of Compound 8 (RNV-125) on body weight in collage induced arthritis in mice

DETAILED DESCRIPTION OF THE INVENTION

Figure 18:
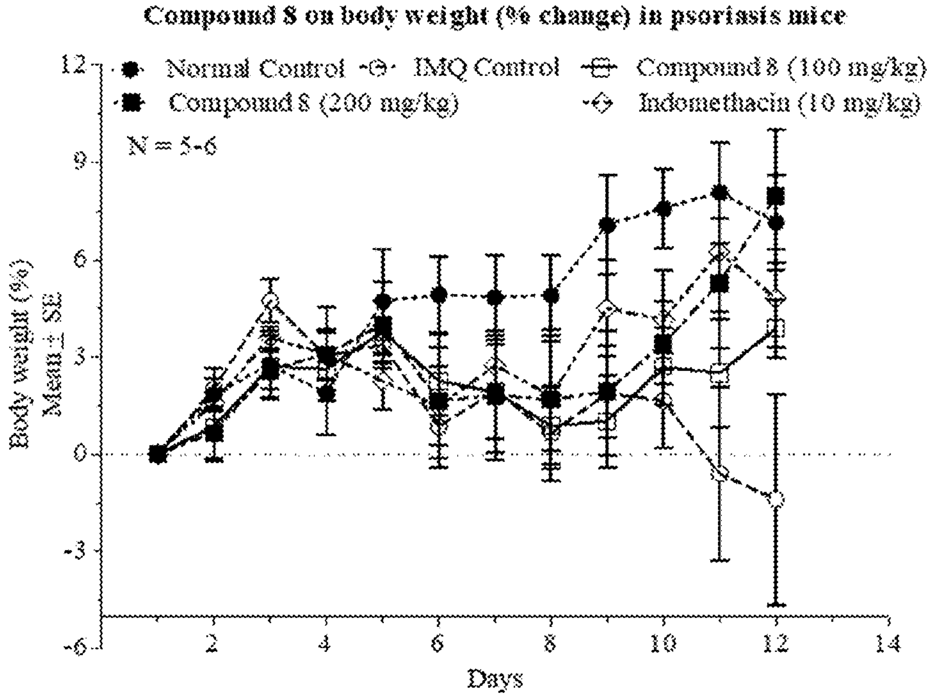
FIG. 18 shows the effect of Compound 8 (RNV-125) at 100 and 200 mg/kg on body weight in psoriatic mice.

A main embodiment is the compound below:

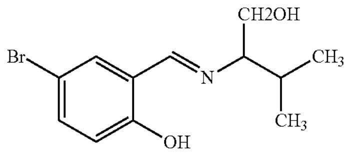

having the following IUPAC name:

4-Bromo-2-[(1-hydroxymethyl-2-methyl-propylimino)-methyl]-phenol and designated by the applicants as "RNV-125", also referred to as "COMPOUND 8".

A second embodiment of the present invention relates to a molecule structurally similar to RNV-125, but having a carboxyl group (—COOH) instead of a hydroxymethyl group (—CHOH) attached to N. This has been designated by the applicants as RNV-124 also referred to as "COMPOUND 7", having the IUPAC name:

2-[(5-Bromo-2-hydroxy-benzylidene)-amino]-3-methyl-butyric acid and having the structural formula:

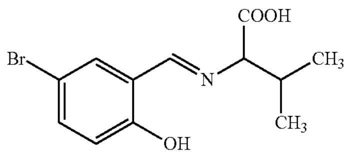

The present invention also relates to a process for the preparation and the therapeutic use of said novel compounds or their derivatives, analogues, tautomeric forms etc.

RNV-125 is an orally active (and therefore orally deliverable) small molecule derived from natural sources and engineered to enhance certain bioactive and pharmacological activities.

RNV-125 shows strong inhibitory effects on inflammatory markers such as TNF-α, IL-1β and IL-6. It is a cytokine antagonist.

There are no orally active (and therefore orally deliverable) drugs available in the market for reducing pro-inflammatory cytokines. Therefore, RNV-125 appears to be a novel molecule for the treatment of inflammatory conditions using oral administration.

The profound effect of this small molecule with approximately 90% inhibition of cytokines makes it an unexpected lead molecule for the development of a new class of orally active cytokine inhibitor.

The applicants have systematically carried out a number of pre-clinical assays and present a selection of evidence herein.

RNV-125 Effect on LPS-Induced Cytokines: TNF-α, IL-6, IL-1β (Study Report #158)

Data evidencing ex-vivo inhibition of cytokines are provided in FIG. 24 (Report 158).

The study shows the effect of RNV-125 on LPS-induced Cytokines: TNF-α, IL-6, IL-1β. The objective of this study (Report 158) was to study the effect of RNV-125 on three cytokines: TNF-α, IL-6, and IL-1β. Inflammation cytokines are the signalling molecules that trigger any inflammatory reaction. TNF-α is a cytokine that stimulates acute phase inflammation reaction. IL-6 is an interleukin which can act as both pro-inflammatory as well as anti-inflammatory cytokine. IL-1β is another important cytokine that plays a big role in mediating the inflammatory response. The study is carried out by ELISA using the serum isolated after Lipopolysaccharide (LPS) stimulation of inflammation cytokines. A control anti-inflammatory agent indomethacin was used. Other controls include mice that were not stimulated by LPS but given saline and mice stimulated with LPS but no treatment.

This study demonstrates that with RNV-125, the reduction in TNF-α was 84%, reduction in IL-6 was 90%, and reduction in IL-1β was 94%. The effect of RNV-125 was comparable to indomethacin, a known anti-inflammatory compound. From this study, it can be concluded that RNV-125 is an ideal molecule in suppressing TNF-α, IL-6, and IL-1β.

RNV-125 on COX-1 and COX-2 Enzyme Activity and Inhibition (Study Report #157)

The effect of RNV-125 on COX-1 and COX-2 enzymes activity and inhibition was studied in an assay. See FIG. 25. The assay is a colourimetric, ex-vivo assay carried out in a 96 well pate. It measures the peroxidase component of COXs. The peroxidase activity is measured colourimetrically by the appearance of oxidized N,N,N',N'-tetramethyl-p-phenylenediamine (TPMD) at 590 nm.

This study demonstrates the effect of RNV-125 on COX-1 and COX-2 enzyme activity and inhibition was studied. RNV-125 reduced the activity of COX-1 by about 10%. No reduction of COX-2 was observed with RNV-125.

RNV-125 on NF-κB-Inducing Kinase (NIK) Inhibition (Study Report #145)

The theoretical algorithms of molecular docking were used to determine an ideal protein receptor for RNV-125. An in-silico protein-ligand docking approach was used to visualize and evaluate the binding potential for RNV-125 to eight different protein receptors and in twenty different binding sites. These receptors were chosen for their essential role in the production of IL-6.

The results presented in this study demonstrate the potential for RNV-125 to be a small molecule inhibitor that targets the IL-6 production pathway, theoretically as a NIK Type A inhibitor in the non-canonical NF-κB pathway.

RNV-125 on Aspirin-Induced Gastric Bleeding (Study Report #029)

The objective of this study was to observe the effect of RNV-125 on gastric irritation in male Swiss Webster mice. The treatment groups of mice were orally administered RNV-125, aspirin, and indomethacin at 5 mg/kg, 25 mg/kg, and 50 mg/kg. The gastric irritation produced after 6 hours was studied. Stomachs were removed, opened along the greater curvature, and washed in cold saline. Blocks measuring 1 mm×10 mm at right angles to the long axis of the stomach were removed. A second sample at 0.5 cm distal to the first sampling area was also removed. The two samples were fixed in formalin and H and E-stained paraffin of the embedded sections was carried out. The extent of mucosal injury was measured. Using a graded micrometre eyepiece, the overall length of tissue section was measured and the corresponding percentage of length of mucosal surface injured was determined. The number of lines and line length were measured with a square grid.

From this study (#29) it can be concluded that RNV-125, when administered at doses of 5 mg/kg, 25 mg/kg, and 50 mg/kg po, has shown demonstrable effect in the gastric irritation model. From the gross as well as the detailed histopathology it is observed that RNV-125 does not produce any gastric irritation. From the quantitative data on the lines and lesions, it is observed that the lines and lesions produced showing the extent of gastric irritation are almost negligible and comparable to the untreated control.

RNV-125 on Imiquimod-Induced Psoriasis in Swiss Webster Mice (Study Report #167)

The objective of this study was to evaluate the effect of RNV-125 on IMQ-induced psoriasis in male Swiss Webster mice. On the day of the study, the mice were randomized into 5 groups with 4 treatment groups and 1 non-treatment control group. The treatment groups were administered with (1) Group I: Vehicle, (2) Group II: RNV-125 at 100 mg/kg, (3) Group III: RNV-125 at 200 mg/kg, and (4) Group IV: Indomethacin (10 mg/kg).

This study shows that the IMQ control of mice showed a decrease in body weight. The RNV-125 at 100 and 200 mg/kg showed a dose-dependent increase in body weight. The IMQ control group of mice showed an increase in the erythema score. RNV-125 at 100 and 200 mg/kg showed a dose-dependent reversal of the IMQ-induced increase of erythema score. A significant reversal of IMQ-induced increase of erythema was observed with RNV-125 at 200 mg/kg ($P<0.05$). A 212% increase in spleen weight was observed in the IMQ control group of mice, compared with the normal control group of mice. Treatment with RNV-125 at 100 and 200 mg/kg significantly ($P<0.05$) reversed the increase in spleen weights in the IMQ control group of mice. Based on the study results, it is concluded that RNV-125 has the potential to be developed as a drug for the treatment of psoriasis.

RNV-125 in Experimental Autoimmune Encephalomyelitis (EAE) in Male C57BL/6 Mice (Study Report #164)

Multiple sclerosis (MS) is characterized by demyelination, axonal degeneration, and subsequent loss of motor function with lesion formation in the white matter of the brain, spinal cord, and optic nerve. The effect of RNV-125 at 100 mg/kg was evaluated in Experimental autoimmune encephalomyelitis, a mice model of multiple sclerosis is shown.

This study shows decrease in body weight was observed in the EAE control group of mice. RNV-125 did not produce a significant effect on body weight when compared with the EAE control group of mice. An increase in clinical scores was observed in the EAE control group of mice. RNV-125 at 100 mg/kg PO produced a 72% decrease in clinical scores when compared with the EAE control group of mice. Histological evaluation of the spinal cords showed the presence of inflammatory infiltrate in the periphery in the EAE control group mice. Treatment with RNV-125 showed an evaluation of the infiltrate infiltrates. It is concluded that RNV-125 is a potential drug candidate to be developed for the treatment of multiple sclerosis.

RNV-125 in Trinitro Benzene Sulfonic Acid (TNBS) Induced Inflammatory Bowel Disease in Rats (Study Report #159)

The objective of this study was to observe the effect of RNV-125 on body weight and colon weight in rats on a normal diet of 6.2% fat. The treatment groups were administered 0.25% of TNBS in ethanol. The treatment groups of rats were administered RNV-125 at 50 mg/kg/day po. Body weights were measured twice a week for all groups.

In this study, the effect of RNV-125 at 50 mg/kg was studied on TNBS-induced inflammatory bowel disease in male albino rats. Treatment with RNV-125 reversed TNBS-induced decrease in body weight by 10.3%. RNV-125 also reversed the TNBS-induced increase in colon weights by 40%. From this study, it can be concluded that all the RNV molecules have the potential for the treatment of inflammatory bowel disease.

RNV-125 on Collagen-Induced Arthritis in Swiss Webster Mice (Study Report #178)

Rheumatoid arthritis is a disease characterized by synovial hypertrophy and production of pro-inflammatory mediators resulting in chronic inflammation of the joint, progressive destruction of cartilage and bone erosion, with clinical symptoms of limb deformity, chronic pain, and reduced quality of life. Immunization of mice with an emulsion of bovine Type-II collagen with Complete Freund's adjuvant leads to the development of collagen-induced arthritis (CIA) consisting of marked synovitis with cartilage degradation and bone erosion. The objective of this study was to observe the effect of RNV-125 on body weight, clinical scores, paw thickness, and histology on collagen-induced arthritis in Swiss Webster mice.

Treatment with RNV-125 at 100 and 200 mg/kg significantly decreased ($P<0.0001$) the clinical scores of arthritis. RNV-125 at 200 mg/kg significantly deceased ($P<0.01$) the paw thickness. Histological evaluation showed that treatment with RNV-125 at 200 mg/kg caused a robust repair of articular joint surface with preserved capsule thickness. It is concluded that RNV-125 has the potential to be developed for the treatment of rheumatoid arthritis.

RNV-125 in Adjuvant Arthritis in Lewis Rats (Study Report #150)

The objective of this study was to observe the effect of RNV-125 on body weight, clinical scores, number of inflamed paws, and arthritic index in Lewis rats on a normal diet of 6.2% fat. The development of arthritis was observed daily from the 12th day following immunization. The treatment groups rats were randomized into various groups: Adjuvant control treated with vehicle, RNV-125 at 50 mg/kg po, and Indomethacin at 1 mg/kg po. A group of normal, non-immunized rats was included as normal control.

Treatment with RNV-125 reversed the body weight decrease in the adjuvant control group by 14%. RNV-125 significantly decreased (P<0.0003) the clinical scores by 35%. RNV-125 significantly decreased (P<0.0005) the arthritic index by 36%. No effect was observed in the number of paws afflicted with arthritic symptoms. From this study it can be concluded that RNV-125 has the potential to be developed for the treatment of rheumatoid arthritis.

RNV-125 in Dextran Sodium Sulfate Induced Inflammatory Bowel Disease (Study Report #148)

The objective of this study was to observe the effect of RNV-125 on body weight, disease activity index (DAI), and colon length in C57BL/6 mice. The mice were randomized into treatment and vehicle groups. The treatment groups were administered 3% DSS (w/v) in the drinking water. The vehicle group was administered potable water. The treatment group of mice was administered RNV-125 at 50 mg/kg/day PO. Body weights were measured and faeces were observed for stool consistency and diarrhoea and also tested for occult blood in all groups. At the end of the study, the colon length was measured and the DAI was calculated for each mouse. The effect of RNV-125 was studied in Dextran Sodium Sulfate (DSS)-induced model of Intestinal Bowel Disease in male C57BL/6 mice. Treatment with RNV-125 improved the DSS-induced decrease in body weight by 13.2%. RNV-125 showed a 29% decrease in the disease activity index. RNV-125 also prevented the decrease in colon length by 9%. From this study, it can be concluded that RNV-125 has the potential to be developed for the treatment of inflammatory bowel disease.

RNV-125 on Carrageenan-Induced Paw Edema & Thickness in Rats (Study Report #147)

In chronic conditions like low back pain, myositis, myofascial pain, and fibromyalgia, muscle pain is one of the major clinical manifestations. Pain models that involve muscle insult closely resemble many clinical pain syndromes. Carrageenan-induced paw oedema is an inflammatory model of pain resembling myositis and tendonitis. An acute phase of inflammation and hyperalgesia initially occurs unilaterally (0 to 1 hour), followed by a chronic phase of inflammation where the hyperalgesia spreads to the contra-lateral hind limb. The objective of this study was to determine the effects of RNV-125 on carrageenan-induced hind paw oedema and thickness in rats.

This study reports the effects of RNV-125 on carrageenan-induced hind paw oedema and paw-thickness in rats. Treatment with the positive control indomethacin or RNV-125 caused a significant decrease in oedema compared with the vehicle group, which were sustained at 4 hours. Treatment with RNV-125 caused a significant decrease in paw thickness compared with the vehicle group, which was sustained at 4 hours. It is concluded that RNV-125 is a potential drug candidate which may be developed for the treatment of inflammation.

RNV-125 on Carrageenan-Induced Paw Volume in Rats (Study Report #161)

The effect of RNV-125 was determined on carrageenan-induced hind paw edema in rats. Carrageenan-induced paw oedema is an inflammatory model of pain resembling myositis and tendonitis. An acute phase of inflammation and hyperalgesia initially occurs unilaterally (0 to 1 hour), followed by a chronic phase of inflammation where the hyperalgesia spreads to the contra-lateral hind limb. Oedema was induced in the right hind paw of male albino rats by injecting carrageenan. The left hind paw served as control. Oedema was measured using a volume-displacement plethysmometer at 1, 2, and 4 hours.

In conclusion, this study shows that treatment with the positive control indomethacin or RNV-125 caused a significant decrease in edema which were maintained at 4 hours. It is concluded that RNV-125 is a potential drug candidate for further development as an anti-inflammatory agent.

Summary of Unexpected Results for RNV-125

RNV-125 ("Compound 8") is an orally active small molecule. The compound shows strong inhibitory effects on inflammatory markers such as TNF-α, IL-1β and IL-6. There is no report of orally active drugs available in the market for reducing pro-inflammatory cytokines. Therefore, RNV-125 appears to be a novel molecule for the treatment of inflammatory conditions. The profound effect of this small molecule with approximately 90% inhibition of cytokines makes it an unexpected lead molecule for the development of a new class of orally active cytokine inhibitor.

Biological Activity (Unexpected Results) for RNV-124 (Compound 7)

Figure 19:
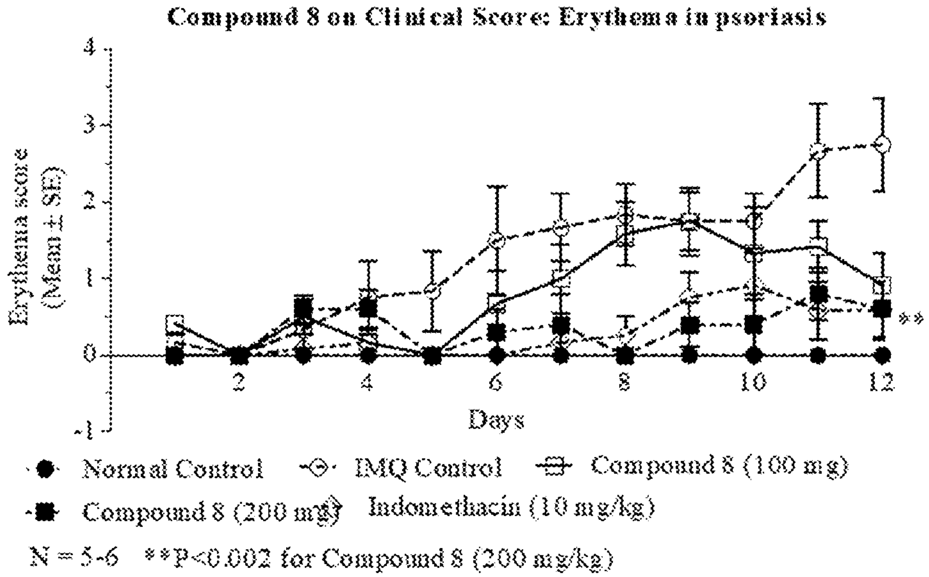
FIG. 19 clinical score erythema
Figure 20:
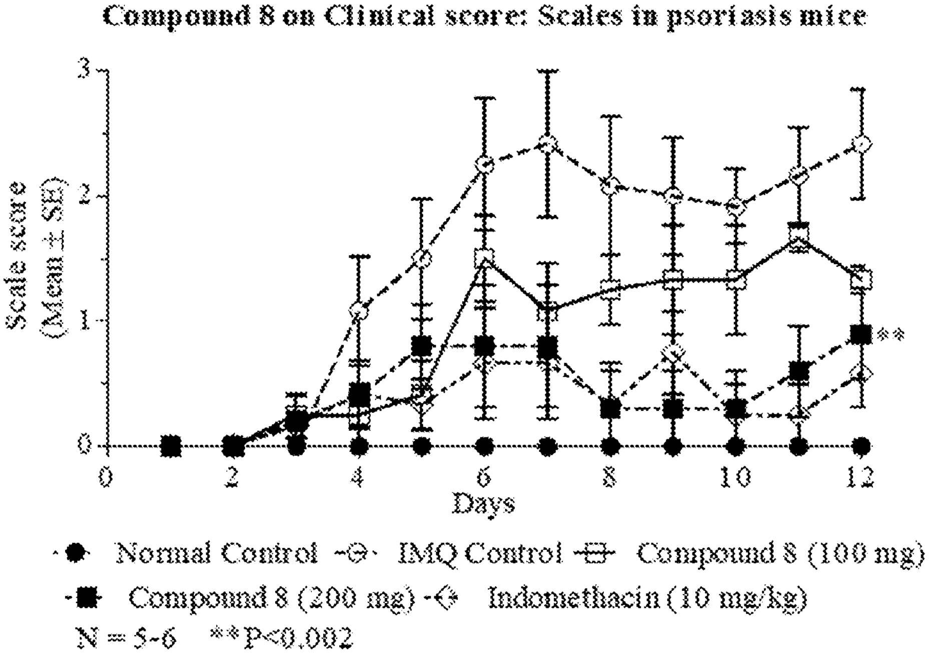
FIG. 20 clinical score scales
Figure 21:
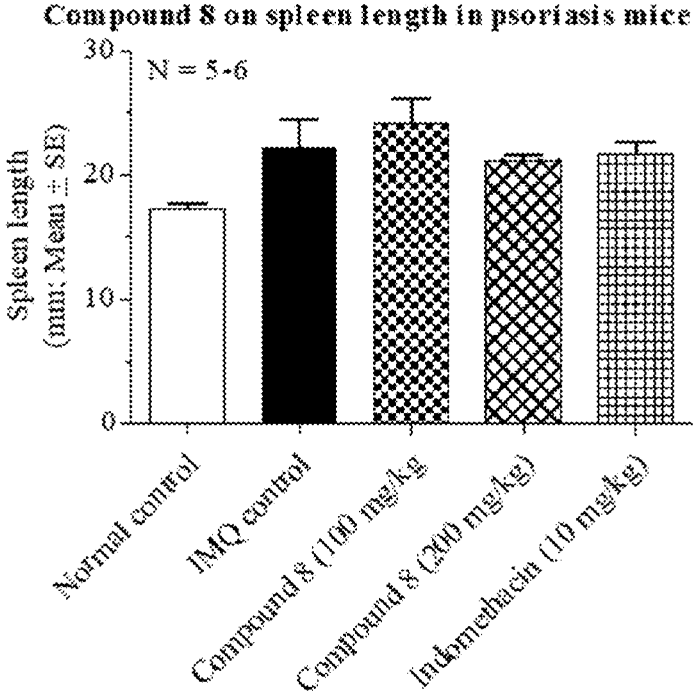
FIG. 21 spleen length
Figure 28B:
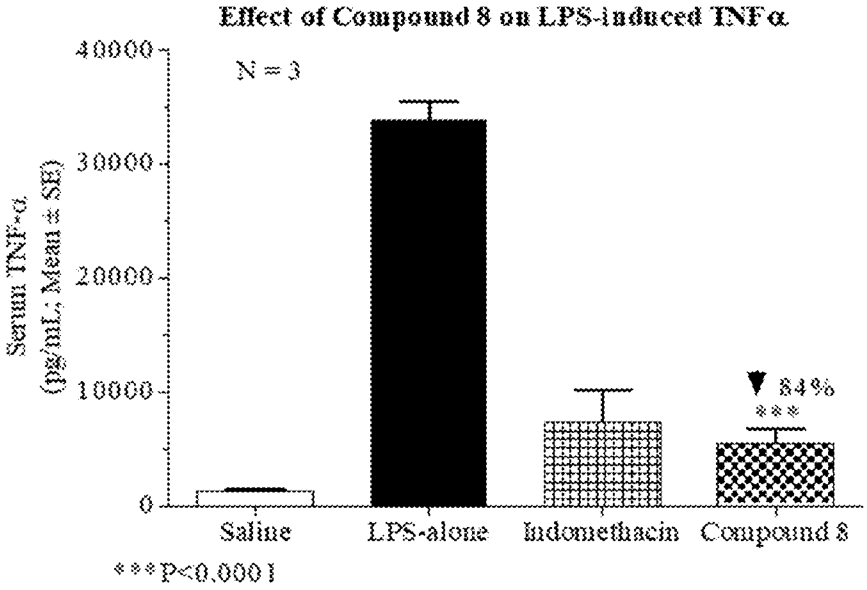
FIG. 28B shows that the group of mice administered with Compound 8 showed (RNV-125) an 84% decrease in TNF-α.
Figure 29A:
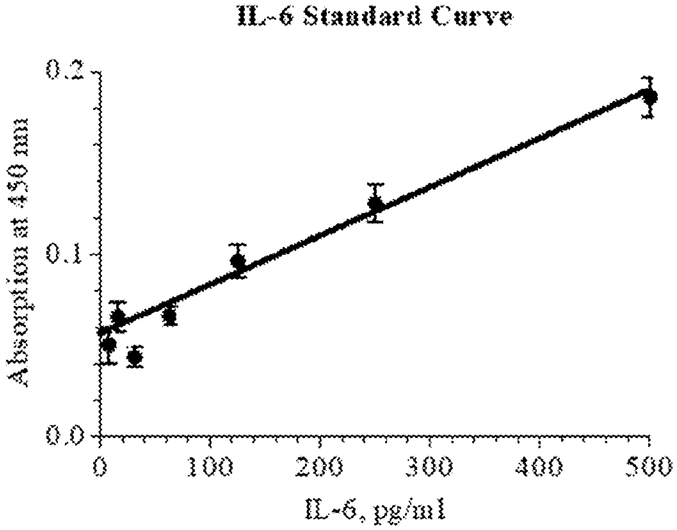
FIG. 29A shows the effect of RNV-125 on IL-6 with its corresponding standard curve.
Figure 29B:
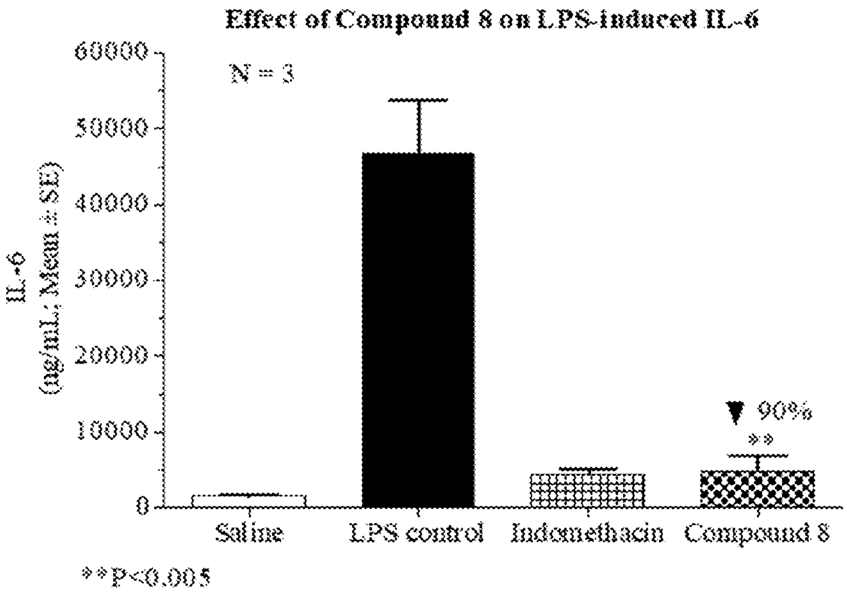
FIG. 29B shows that the group of mice administered with Compound 8 showed (RNV-125) an 90% decrease in IL-6.
Figure 30A:
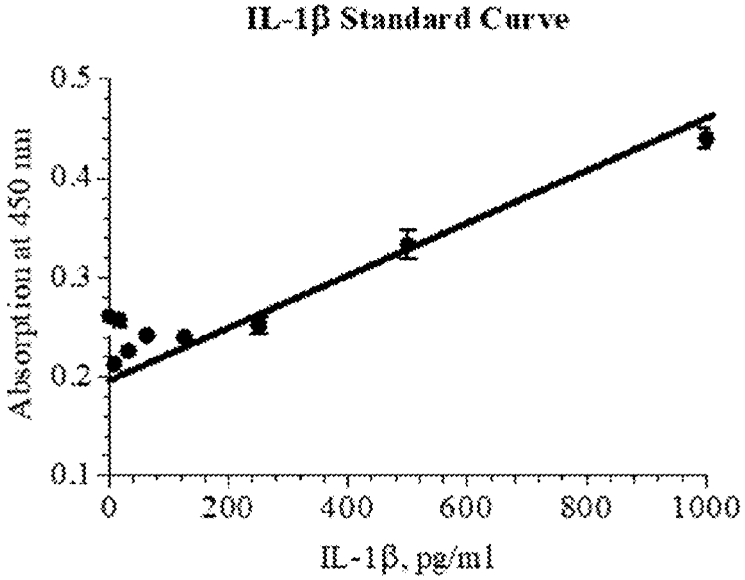
FIG. 30A shows the effect of RNV-125 on IL-1B with its corresponding standard curve.
Figure 30B:
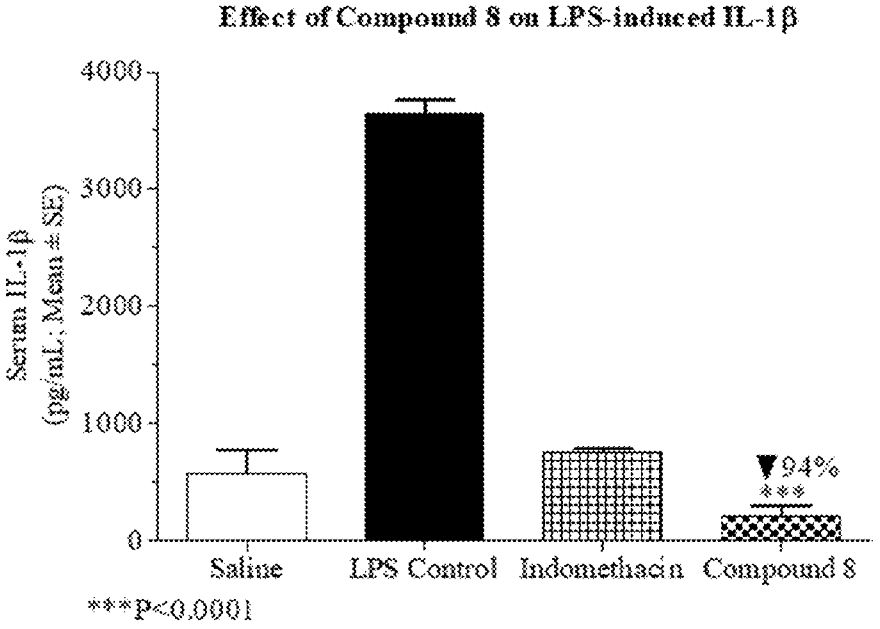
FIG. 30B shows that the group of mice administered with Compound 8 showed (RNV-125) an 94% decrease in IL-1β.
Figure 35:
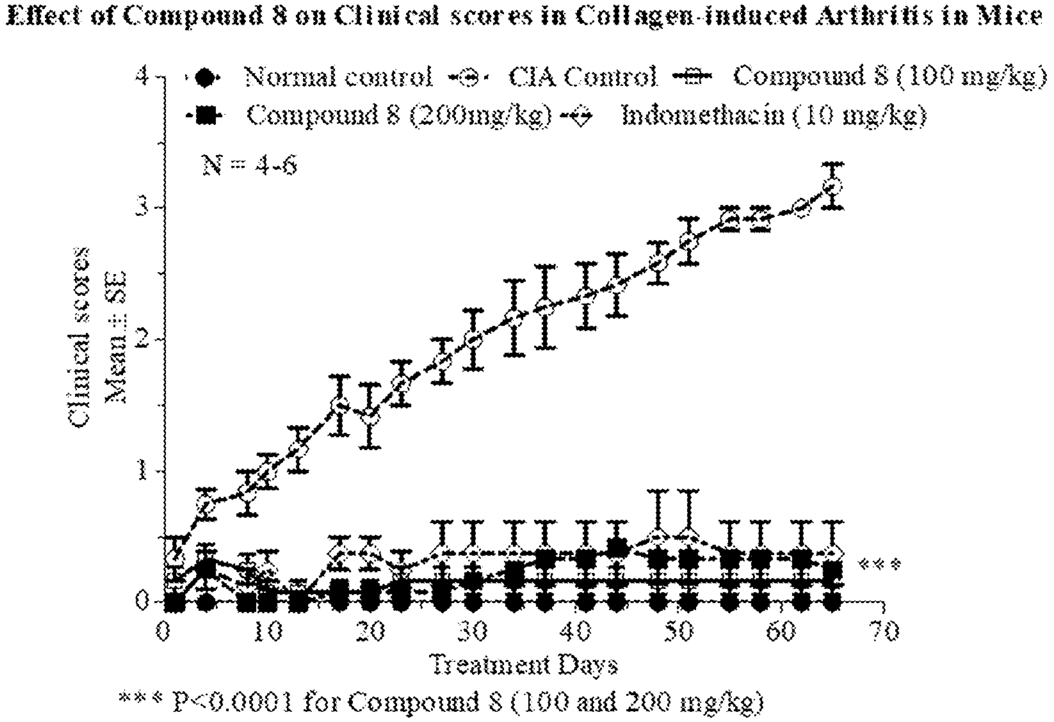
FIG. 35 shows that Compound 8 (RNV-125) at 100 and 200 mg/kg produced a significant ($P<0.0001$) decrease in clinical scores in collaged induced arthritis in mice
Figure 36:
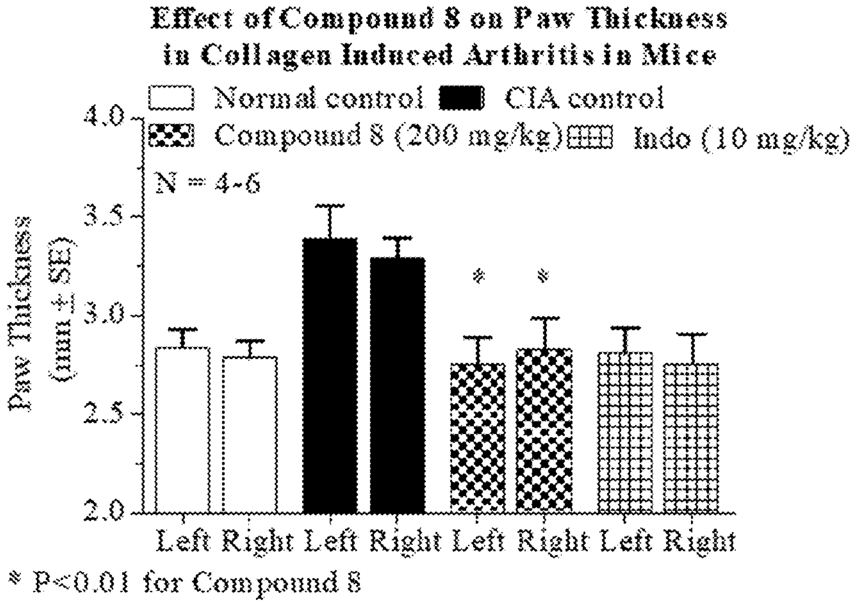
FIG. 36 shows that Compound 8 (RNV-125) at 200 mg/kg produced a significant ($P<0.01$) decrease in the left and right paw thicknesses in collagen induced arthritis in mice
Figure 37:
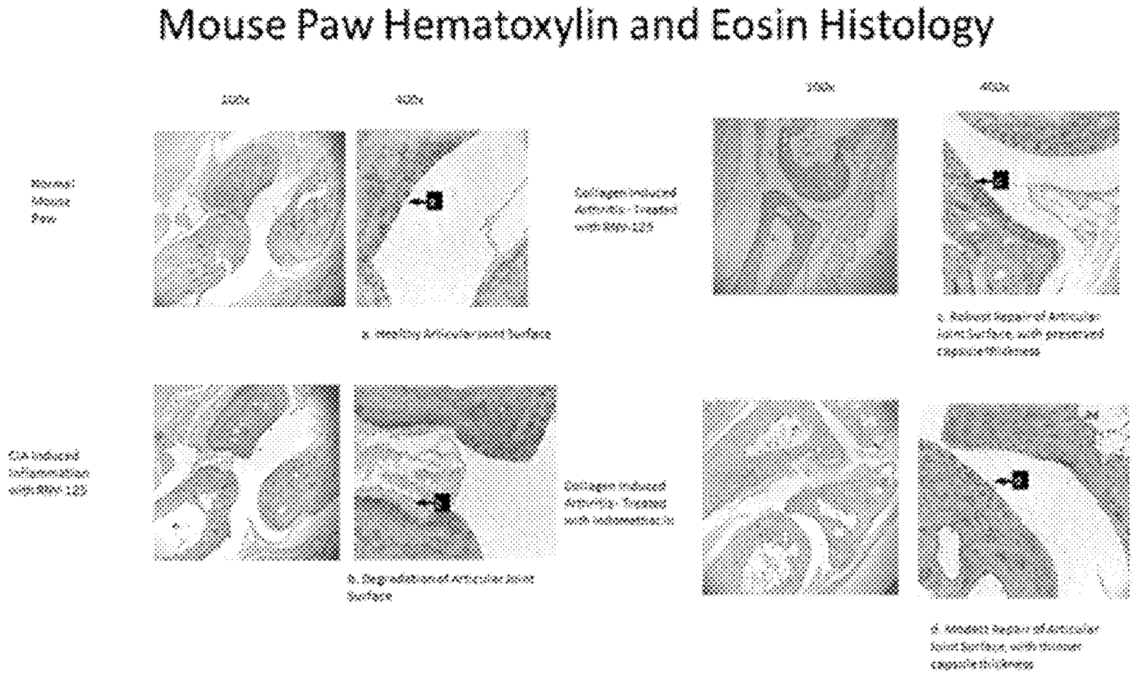
FIG. 37 shows the effect of Compound 8 (RNV-125) on Hematoxylin and Eosin histology in collagen induced arthritis in mice
Figure 38:
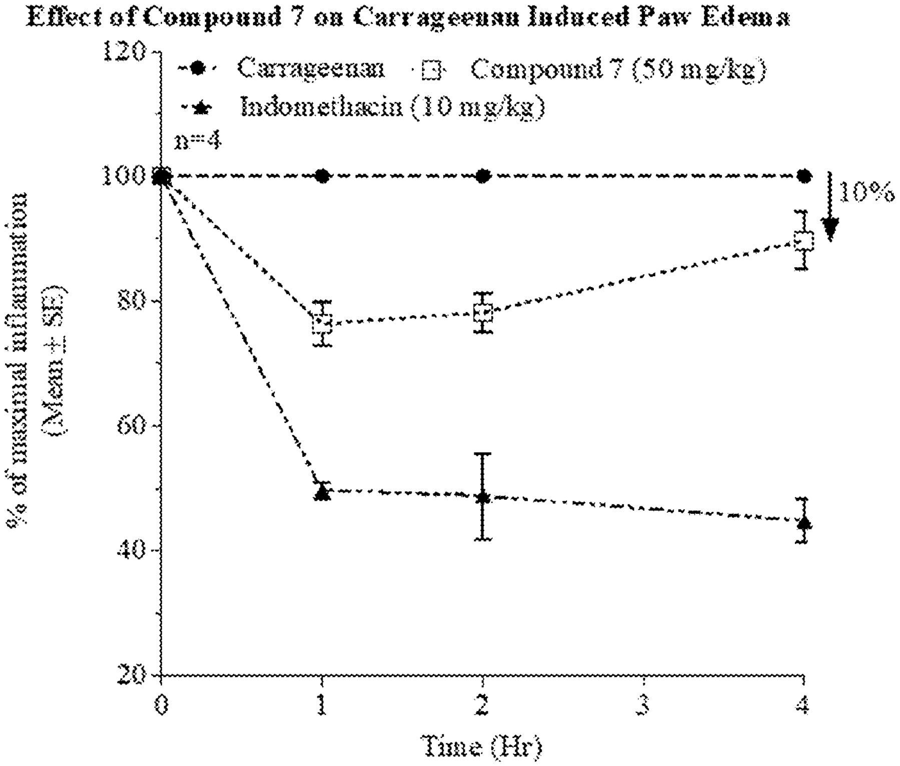
FIG. 38 shows that the group of rats administered with Compound 7 (RNV-124) exhibited a 10% decrease in carrageenan-induced inflammation.
Figure 39:
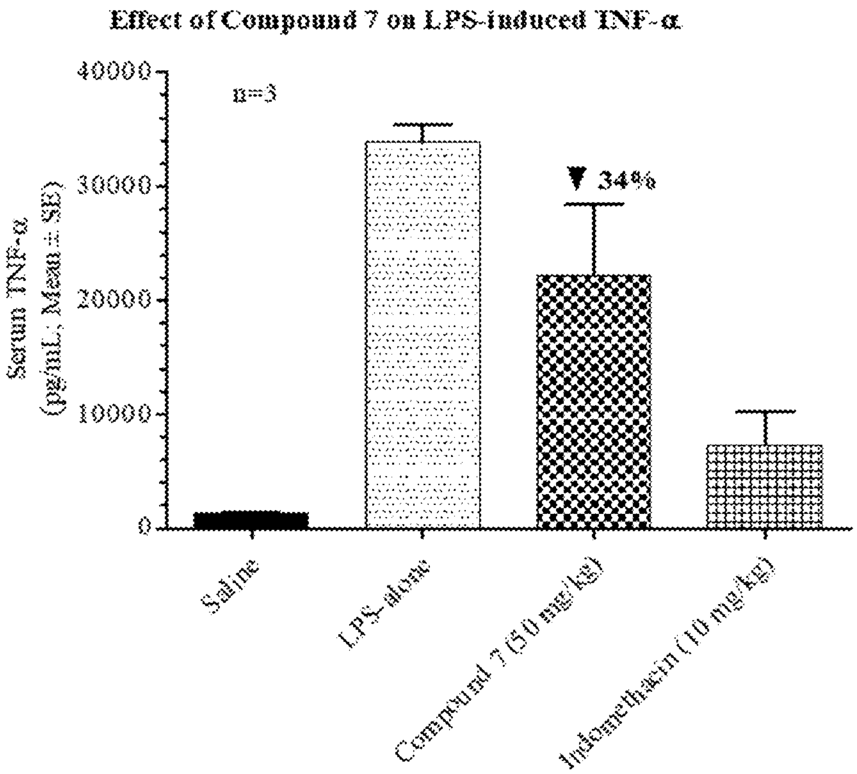
FIG. 39 shows that mice administered with RNV-124 (Compound 7) showed a 34% decrease in TNF-α.
Figure 40:
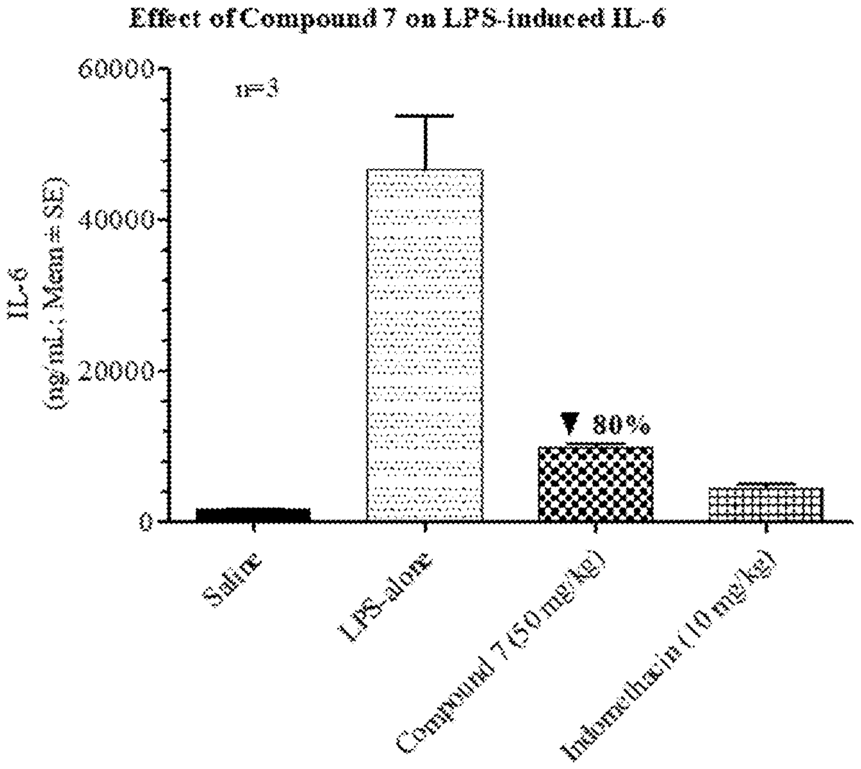
FIG. 40 shows that mice administered with RNV-124 (Compound 7) showed an 80% decrease in IL-6.
Figure 41:
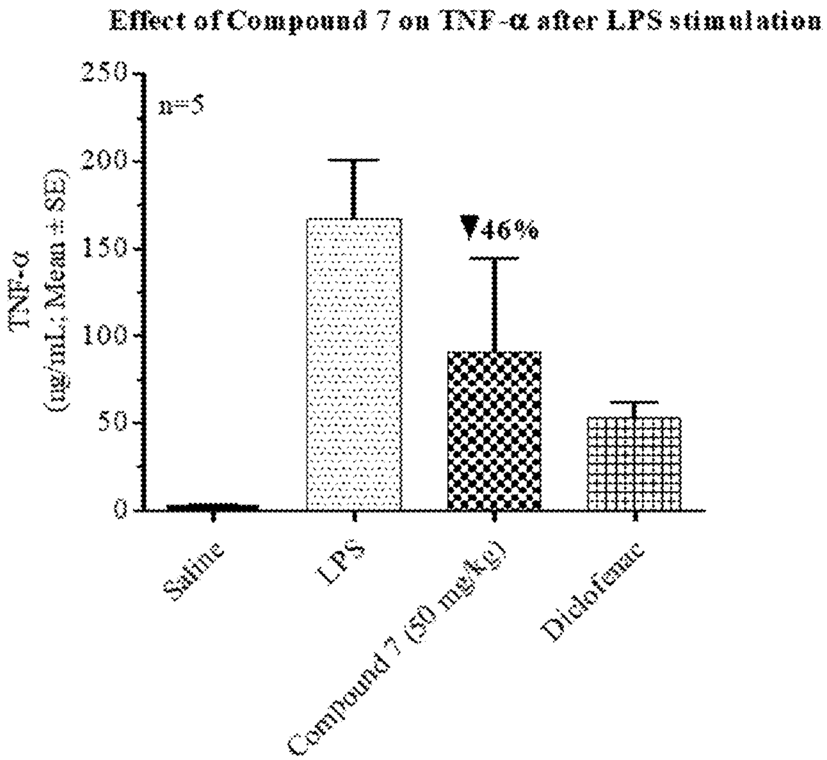
FIG. 41 shows that mice administered with RNV-124 (Compound 7) showed a 46% decrease in TNF-α from the LPS group.

RNV-124 (2-[(5-Bromo-2-hydroxy-benzylidene)-amino]-3-methyl-butyric acid) shows strong biological activity when administered orally. In vivo data (see the FIGS. 26-19) shown 34% decrease in TNF-α (FIGS. 23A and 24), 80% decrease in IL-6 (FIG. 23B), and 68% decrease in IL-18 (FIG. 23C) from the LPS group.

Formulations of the Compounds of the Invention

The formula of the compounds of the invention include (but are not limited to) those listed below.

One key molecule of the invention is "RNV-125", also referred to as "COMPOUND 8", having the IUPAC name: 4-Bromo-2-[(1-hydroxymethyl-2-methyl-propylimino)-methyl]-phenol; and having the structural formula:

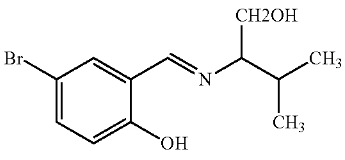 [SMILES: CC(C)C(CO)/N=C/c1cc(Br)ccc1O]

The present invention also relates to a process for the preparation and the therapeutic use of any of said novel compounds or their analogues, their tautomeric forms etc.

Another molecule of the invention is very structurally similar to RNV-125, and has been designated by the applicants as RNV-124 also referred to as "COMPOUND 7", having the IUPAC name: 2-[(5-Bromo-2-hydroxy-benzylidene)-amino]-3-methyl-butyric acid (Compound 7); and having the structural formula:

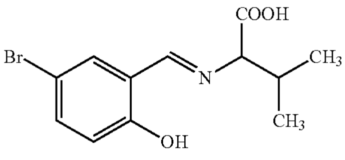 [SMILES: CC(C)C(/N=C/c1cc(Br)ccc1O)C(=O)O]

The invention encompasses derivatives, pharmaceutically acceptable salts, esters, solvates, hydrates, prodrugs, and polymorphs thereof, including all stereoisomeric forms (e.g., enantiomers, diastereomers), tautomers, and isotopically enriched forms of the compounds. Unless otherwise specified, such references encompass both racemic mixtures and individual enantiomers or diastereomers. Derivatives of the compounds include compounds structurally modified by substitution, elimination, or addition of one or more chemical groups, provided such derivatives retain the essential pharmacological activity. Preferred salts for the compounds listed above are hydrochloride, hydrobromide, sodium, potassium, or magnesium.

According to another feature of this present invention, the invention provides a process for the preparation of the compound represented by the formula I, wherein all symbols are as defined as earlier, as shown in Scheme 1.

Scheme 1

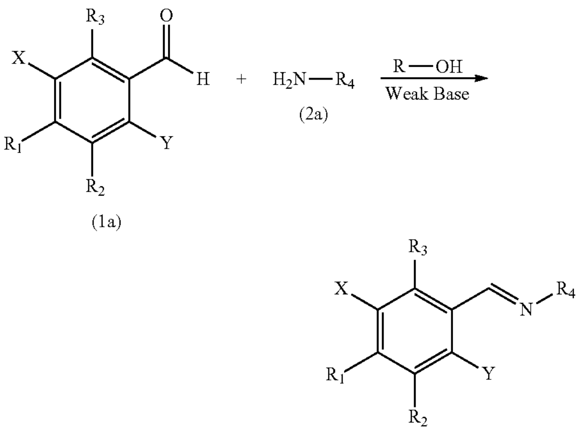

(1a) (2a) (3a)

The reaction of a compound of general formula (1a) with a compound of general formula (2a) to produce a compound of the general formula (3a) may be carried out in an inert atmosphere which may be maintained by using inert gases such as nitrogen, argon or helium. The reaction may be carried out in a polar protic solvent like alcohols, preferably methanol or ethanol and in the presence of weak bases like DEA, TEA, Isopropylamine, pyridine, pipridine and the like, but more preferably with a base like TEA.

The temperature of the reaction may range between 40 to 80° C., optimally between 60 to 80° C. and the duration may extend between 1 to 10 hours. The schiff base thus formed may be precipitated or could be extracted after suitable workup procedures such as water quenching. The resultant molecule is the halogenated benzylidine derivative of general formula (3a) where the groups have been defined earlier.

The invention is explained in detail in the EXAMPLES given below which are provided by way of illustration only and therefore should not be construed to limit the scope of the invention.

Example 1

Synthesis of 2-[(5-Bromo-2-hydroxy-benzylidene)-amino]-3-methyl-butyric acid ("COMPOUND 7")

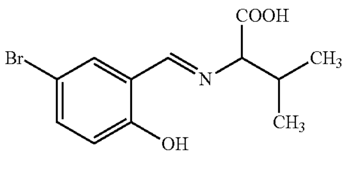 [SMILES: CC(C)C(/N=C/c1cc(Br)ccc1O)C(=O)O]

Step (i)

Synthesis of Valine Methyl Ester Hydrochloride

Valine (50.0 g) was taken in a clean and dry round bottom flask and methanol (150 ml) was added. Thionyl chloride (34.50 ml) was introduced in to the reaction mixture and it was refluxed at 70-80° C. for 6 hours with constant stirring. The excess solvent was then removed by distillation and the solid product obtained was stored under nitrogen. Yield—75.0 g Step (ii)

Valine methyl ester hydrochloride (75.0 g) and 5-bromo salicaldehyde (50.0 g) were taken in a clean and dry round bottom flask and methanol (250 ml) was added with constant stirring. Triethylamine (50 ml) was introduced in to the mixture and it was refluxed for 8 hours at 65-70° C. Molecular sieves were also added to scavenge the water produced during the reaction. The reaction mass was then dissolved in acetone (200 ml) and filtered to remove the undissolved material. A solid precipitate was obtained when water (500 ml) was added to the filtrate. This was then filtered and dried. Yield—54.6 g.

Step (iii)

2-[(5-Bromo-2-hydroxy-benzylidene)-amino]-3-methyl-butyric acid methyl (9.0 g) was taken in a clean and dry round bottom flask and NaOH solution (3.69 g/120 ml) was added to it with constant stirring. Acetone (90 ml) was added and the mixture was maintained at room temperature for 3 hours. The reaction mixture was then cooled to 25° C. and the pH was brought to 5.5 using 1:1 HCl solution. The precipitated solid was filtered, washed with water followed by hexane and dried. Yield 5.80 g. NMR—10.21 (1H, s), 8.13 (1H, s), 6.65-7.62 (Aromatic), 5.0 (1H, s), 3.89 (1H, d), 2.04 (1H, m), 1.12 (6H, d)

Example 2

Synthesis of 2-[(5-Bromo-2-hydroxy-benzylidene)-amino]-3-methyl-butyric acid ("COMPOUND 8")

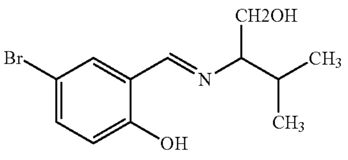 [SMILES: CC(C)C(CO)/N=C/c1cc(Br)ccc1O]

Step (i)

Synthesis of valinol·Valine (11.7 g) was taken in a clean and dry round bottom flask and tetrahydrofuran (100 ml) was added with constant stirring. Boron trifluoride ethyl ether complex 14.2 ml) and borane dimethylsulphide (10 ml) were added and the reaction mixture was refluxed at 40-50° C. for 4 hours. The reaction mixture was acidified with 0.5N HCl and the THF layer was separated and washed twice with water. The solvent was then dried over sodium sulphate and evaporated to obtain the product. Yield 8.0 g.

Step (ii) Valinol (10 g) and 5-bromo salicaldehyde (4.0 g) were taken in a clean and dry round bottom flask and methanol (100 ml) was added with constant stirring. TEA (1.0 ml) was added and the mixture was refluxed for 4 hours at 65-70° C. The excess solvent was then removed by distillation and the crude product was dissolved in water (150 ml). Chloroform was used to extract the product from the solution and the separated organic layer was dried over sodium sulphate and then removed under reduced pressure to obtain the final product. Yield—5.2 g. NMR—6.65-7.62 (Aromatic), 5.0 (1H, s), 3.89 (1H, d), 2.04 (1H, m), 1.12 (6H, d)

The invention claimed is:

1. A method for treating inflammation, the method comprising the oral administration to a subject in need thereof a clinically effective dose of the following compound:

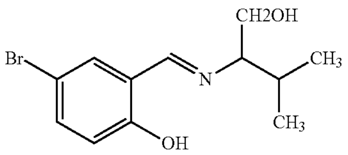

named 4-Bromo-2-[(1-hydroxymethyl-2-methyl-propylimino)-methyl]-phenol (RNV-125).

2. A method for treating inflammation, the method comprising the oral administration to a subject in need thereof a clinically effective dose of the following compound:

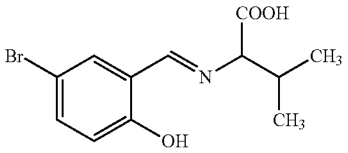

named 2-[(5-Bromo-2-hydroxy-benzylidene)-amino]-3-methyl-butyric acid (RNV-124).

3. The method of claim 1 wherein said method results in a measurable reduction of inflammation and a decrease in plasma concentration of TNF-α.

4. The method of claim 1 wherein said method results in a measurable reduction of inflammation and a decrease in plasma concentration of IL-6.

5. The method of claim 1 wherein said method results in a measurable reduction of inflammation and a decrease in plasma concentration of IL-1β.

6. The method of claim 1 wherein said method results in a measurable reduction of inflammation and a decrease in arthritic symptoms as measured by the Arthritic Index.

7. The method of claim 1 wherein said method results in a decrease in plasma concentration of TNF-α, IL-1β, and IL-6.

8. The method of claim 2 wherein said method results in a decrease in plasma concentration of TNF-α.

9. The method of claim 2 wherein said method results in a decrease in plasma concentration of IL-6.

10. The method of claim 2 wherein said method results in a decrease in plasma concentration of IL-1β.

11. The method of claim 2 wherein said method results in a decrease in plasma concentration of TNF-α IL-6 and IL-1β.

* * * * *